US011766403B2

(12) United States Patent
Moudgil et al.

(10) Patent No.: US 11,766,403 B2
(45) Date of Patent: Sep. 26, 2023

(54) PEPTIDE-TARGETED LIPOSOMAL DELIVERY FOR TREATMENT, DIAGNOSIS, AND IMAGING OF DISEASES AND DISORDERS

(71) Applicants: University of Maryland, Baltimore, Baltimore, MD (US); The United States Government as represented by the Department of Veterans Affairs, Washington, DC (US)

(72) Inventors: Kamal D. Moudgil, Silver Springs, MD (US); Rakeshchandra R. Meka, Halethorp, MD (US)

(73) Assignees: University of Maryland, Baltimore, Baltimore, MD (US); The United States Government as represented by the Department of Veterans Affairs, Washington, DC (US)

(*) Notice: Subject to any disclaimer, the term of this patent is extended or adjusted under 35 U.S.C. 154(b) by 0 days.

(21) Appl. No.: 16/825,371

(22) Filed: Mar. 20, 2020

(65) Prior Publication Data
US 2020/0297633 A1 Sep. 24, 2020

Related U.S. Application Data

(60) Provisional application No. 62/821,750, filed on Mar. 21, 2019.

(51) Int. Cl.
| | |
|---|---|
| A61K 9/127 | (2006.01) |
| A61K 38/08 | (2019.01) |
| A61K 47/42 | (2017.01) |
| A61K 47/64 | (2017.01) |
| A61K 47/69 | (2017.01) |
| C07K 7/06 | (2006.01) |
| A61P 19/02 | (2006.01) |

(52) U.S. Cl.
CPC ............ *A61K 9/1271* (2013.01); *A61K 38/08* (2013.01); *A61K 47/42* (2013.01); *A61K 47/64* (2017.08); *A61K 47/6911* (2017.08); *C07K 7/06* (2013.01); *A61P 19/02* (2018.01)

(58) Field of Classification Search
CPC ...... A61K 9/1271; A61K 38/08; A61K 38/12; A61K 47/42; A61K 47/64; A61K 47/6911; C07K 7/06; C07K 7/64
See application file for complete search history.

(56) References Cited

PUBLICATIONS

Meka et al. Peptide-targeted liposomal delivery of dexamethasone for arthritis therapy. Nanomedicine.Apr. 2, 2019, vol. 14, No. 11, pp. 1455-1469. (Year: 2019).*
Firestein GS, "Evolving concepts of rheumatoid arthritis" Nature, 2003, 423:356-361.
Harris ED, "Rheumatoid arthritis. Pathophysiology and implications for therapy", N. Engl. J. Med., 1990, 322:1277-1289.
Gibofsky A, "Current therapeutic agents and treatment paradigms for the management of rheumatoid arthritis", Am J Manag Care, 2014, 20:S136-144 (2014).
Curtis JS et al., "Use of biologies in rheumatoid arthritis: current and emerging paradigms of care", Clin. Ther., 2011, 33:679-707.
Kim GW et al., "IL-6 inhibitors for treatment of rheumatoid arthritis: past, present, and future", Arch. Pharm. Res., 2015, 38:575-584.
Bui VL et al., "Cytokine targeting in rheumatoid arthritis", Clinical immunology, 2019, 206:3-8.
Sfikakis PP et al., "Towards the next generation of anti-TNF drugs", Clinical Immunology, 2011, 141:231-235.
Ramiro S et al., "Safety of synthetic and biological DMARDs: a systematic literature review informing the 2016 update of the EULAR recommendations for management of rheumatoid arthritis", Annals of the rheumatic diseases, 2017, 76:1101-1136.
Allen TM et al., "Liposomal drug delivery systems: from concept to clinical applications", Advanced drug delivery reviews, 2013, 65:36-48.
Koning GA et al., "Targeting of angiogenic endothelial cells at sites of inflammation by dexamethasone phosphate-containing RGD peptide liposomes inhibits experimental arthritis", Arthritis and rheumatism, 2006, 54:1198-1208.
Ruoslahti E et al., "Targeting of drugs and nanoparticles to tumors", The Journal of cell biology, 2010, 188:759-768.
Sercombe L et al., "Advances and Challenges of Liposome Assisted Drug Delivery", Frontiers in pharmacology, 2015, 6:286.
Yang M et al., "Nanotherapeutics relieve rheumatoid arthritis", Journal of controlled release, 2017, 252:108-124.
Ferrari M et al., "Trojan horses and guided missiles: targeted therapies in the war on arthritis" Nature reviews, 2015, 11:328-337.
Qi R et al., "Folate Receptor-Targeted Dendrimer-Methotrexate Conjugate for Inflammatory Arthritis", Journal of biomedical nanotechnology, 2015, 11:1431-1441.

(Continued)

*Primary Examiner* — Jeffrey E. Russel
(74) *Attorney, Agent, or Firm* — Riverside Law LLP

(57) ABSTRACT

The present invention relates in part to compositions for targeted delivery of an agent and agent delivery systems comprising a novel tissue-targeting peptide ligand (CK-PFDRALC) (SEQ ID NO: 1) named ART-2. In certain aspects, the ART-2-coated liposomes encapsulating an agent, such as a therapeutic agent, diagnostic agent, imaging agent, or any combination thereof, were more effective in inhibiting, diagnosing, or imaging a disease or disorder, such as an arthritis progression, than control, despite a comparable safety profile.

22 Claims, 14 Drawing Sheets

Specification includes a Sequence Listing.

(56) References Cited

PUBLICATIONS

Yang M et al., "Treatment of collagen-induced arthritis by activated macrophage-targeted dextran-methotrexate/folate conjugate", Nanomedicine: Nanotechnology, Biology and Medicine, 2018, 14:1815-1816.
Ruoslahti E, "Peptides as targeting elements and tissue penetration devices for nanoparticles", Advanced materials, 2012, 24:3747-3756.
Teesalu T et al., "Tumor-penetrating peptides", Frontiers in oncology, 2013, 3:216.
Perez-Herrero E et al., "Advanced targeted therapies in cancer: Drug nanocarriers, the future of chemotherapy", European journal of pharmaceutics and biopharmaceutics, 2015, 93:52-79.
Zhao G et al., "Molecular targeting of liposomal nanoparticles to tumor microenvironment", International journal of nanomedicine, 2013, 8:61-71.
Vanniasinghe AS et al., "Targeting fibroblast-like synovial cells at sites of inflammation with peptide targeted liposomes results in inhibition of experimental arthritis", Clinical immunology, 2014, 151:43-54.
Poh S et al., "Folate-conjugated liposomes target and deliver therapeutics to immune cells in a rat model of rheumatoid arthritis", Nanomedicine, 2017, 12:2441-2451.
Nogueira E et al., "Enhancing Methotrexate Tolerance with Folate Tagged Liposomes in Arthritic Mice", Journal of biomedical nanotechnology, 2015, 11:2243-2252.
Look M et al., "Nanogel-based delivery of mycophenolic acid ameliorates systemic lupus erythematosus in mice", The Journal of clinical investigation, 2013, 123:1741-1749.
Ezaki T et al., "Time course of endothelial cell proliferation and microvascular remodeling in chronic inflammation", The American journal of pathology, 2001, 158:2043-2055.
Szekanecz Z et al., "Angiogenesis and its targeting in rheumatoid arthritis", Vascular pharmacology, 2009, 51:1-7.
Szmitko PE et al., "New markers of inflammation and endothelial cell activation: Part I. Circulation", 2003, 108:1917-1923.
Bordag N et al., "Glucocorticoid (dexamethasone)-induced metabolome changes in healthy males suggest prediction of response and side effects", Scientific reports, 2015, 5:15954.
Tsurufuji S et al., "Mechanisms of anti-inflammatory action of dexamethasone: blockade by hydrocortisone mesylate and actinomycin D of the inhibitory effect of dexamethasone on leukocyte infiltration in inflammatory sites", The Journal of pharmacology and experimental therapeutics, 1984, 229:237-243.
Dankers W et al., "1,25(OH)2D3 and dexamethasone additively suppress synovial fibroblast activation by CCR6(+) T helper memory cells and enhance the effect of tumor necrosis factor alpha blockade", Arthritis research & therapy, 2018, 20:212.
Migliore MM et al., "Brain delivery of proteins by the intranasal route of administration: a comparison of cationic liposomes versus aqueous solution formulations", Journal of pharmaceutical sciences, 2010, 99:1745-1761.
Helmy HS et al., "Therapeutic effects of lornoxicam-loaded nanomicellar formula in experimental models of rheumatoid arthritis", International journal of nanomedicine, 2017, 12:7015-7023.
Meka R et al., "Asymmetric cationic lipid based non-viral vectors for an efficient nucleic acid delivery", RSC Advances, 2016, 6:77841-77848.
Yang YH et al., "Peptides targeting inflamed synovial vasculature attenuate autoimmune arthritis", Proceedings of the National Academy of Sciences of the United States of America, 2011, 108:12857-12862.
Rajaiah R et al., "Interleukin-27 and interferon-gamma are involved in regulation of autoimmune arthritis", The Journal of biological chemistry, 2011, 286:2817-2825.
Astry B et al., "Celastrol, a Chinese herbal compound, controls autoimmune inflammation by altering the balance of pathogenic and regulatory T cells in the target organ", Clinical immunology, 2015, 157:228-238.
Moudgil KD et al., "Diversification of T cell responses to carboxy-terminal determinants within the 65-kD heat-shock protein is involved in regulation of autoimmune arthritis", The Journal of experimental medicine, 1997, 185:1307-1316.
Venkatesha SH et al., "Celastrus-derived celastrol suppresses auto-immune arthritis by modulating antigen-induced cellular and humoral effector responses", The Journal of biological chemistry, 2011, 286:15138-15146.
Heo R et al., "Dextran sulfate nanoparticles as a theranostic nanomedicine for rheumatoid arthritis", Biomaterials, 2017, 131:15-26.
Anderson R et al., "Liposomal encapsulation enhances and prolongs the anti-inflammatory effects of water-soluble dexamethasone phosphate in experimental adjuvant arthritis" Arthritis research & therapy, 2010, 12:R147.
Hofkens W et al., "Intravenously delivered glucocorticoid liposomes inhibit osteoclast activity and bone erosion in murine antigen-induced arthritis", Journal of controlled release, 2011, 152:363-369.
Prabhu P, et al., "Investigation of nano lipid vesicles of methotrexate for anti-rheumatoid activity", International journal of nanomedicine, 2012, 7:177-186.
Van Den Hoven JM et al., "Optimizing the therapeutic index of liposomal glucocorticoids in experimental arthritis", International journal of pharmaceutics, 2011, 416:471-477.
Ulmansky R et al., "Glucocorticoids in nano-liposomes administered intravenously and subcutaneously to adjuvant arthritis rats are superior to the free drugs in suppressing arthritis and inflammatory cytokines", Journal of controlled release, 2012, 160:299-305.
Meka RR et al., "Peptide-directed liposomal delivery improves the therapeutic index of an immunomodulatory cytokine in controlling autoimmune arthritis", Journal of controlled release, 2018, 286:279-288.
Meka RR et al., "IL-27-induced modulation of autoimmunity and its therapeutic potential", Autoimmunity reviews, 2015, 14:1131-1141.
Wythe SE et al., "Targeted delivery of cytokine therapy to rheumatoid tissue by a synovial targeting peptide", Annals of the rheumatic diseases, 2013, 72:129-135.
Yang M et al., "Scavenger Receptor-Mediated Targeted Treatment of Collagen-Induced Arthritis by Dextran Sulfate-Methotrexate Prodrug", Theranostics, 2017, 7:97-105.
Zhang R et al., "Treatment of experimental autoimmune uveoretinitis with intravitreal injection of infliximab encapsulated in liposomes", The British journal of ophthalmology, 2017, 101:1731-1738.
Turjeman K et al., "Nano-Drugs Based on Nano Sterically Stabilized Liposomes for the Treatment of Inflammatory Neurodegenerative Diseases", PloS one, 2015, 10:e0130442.
Fuhrmann T et al., "Peptide-functionalized polymeric nanoparticles for active targeting of damaged tissue in animals with experimental autoimmune encephalomyelitis", Neuroscience letters, 2015, 602:126-132.
Gammon JM et al., "Controlled delivery of a metabolic modulator promotes regulatory T cells and restrains autoimmunity", Journal of controlled release, 2015, 210:169-178.
Scindia Y et al., "Anti-alpha8 integrin immunoliposomes in glomeruli of lupus-susceptible mice: a novel system for delivery of therapeutic agents to the renal glomerulus in systemic lupus erythematosus", Arthritis and rheumatism, 2008, 58:3884-3891.
Gaillard PJ et al., "Enhanced brain delivery of liposomal methylprednisolone improved therapeutic efficacy in a model of neuroinflammation", Journal of controlled release, 2012, 164:364-369.

* cited by examiner

Figure 1B
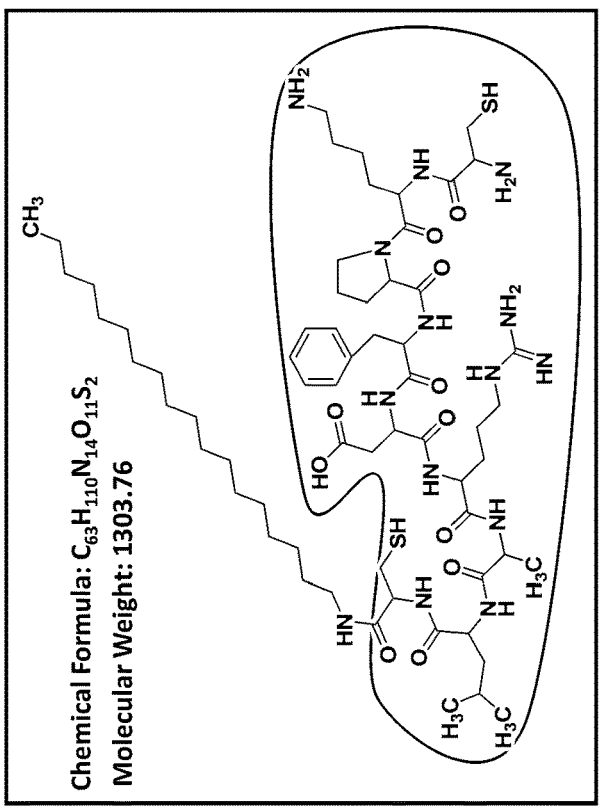
Figure 1A
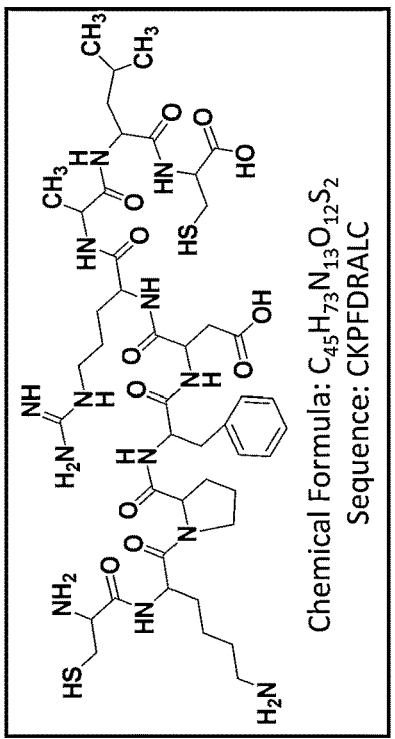
Figure 1

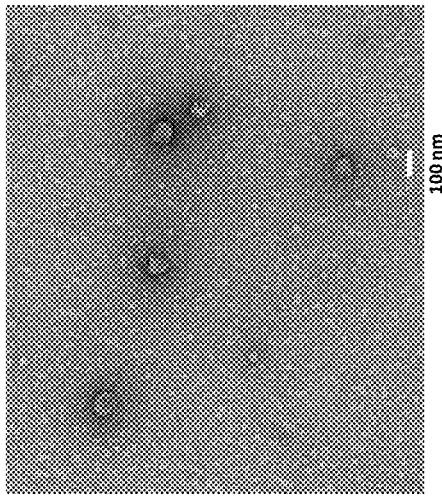
Figure 3A
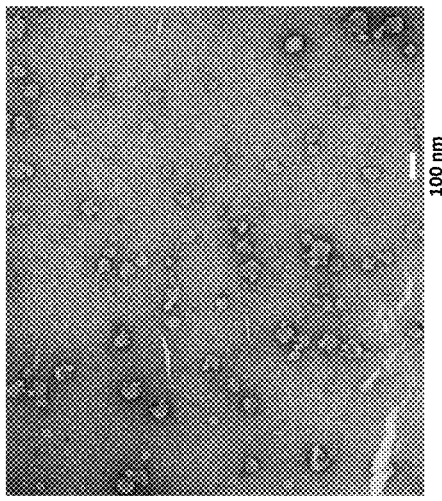
Figure 3C
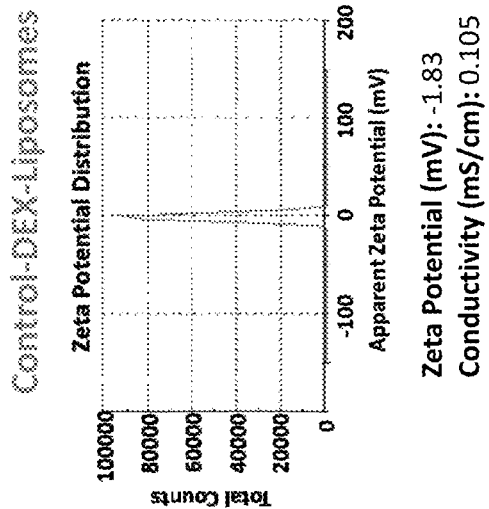
Figure 3B
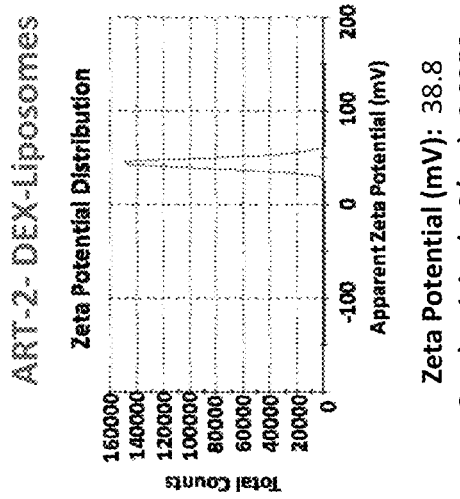
Figure 3D
Figure 3

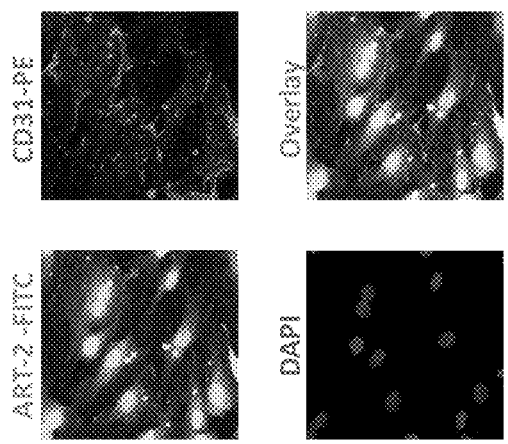
Figure 4B
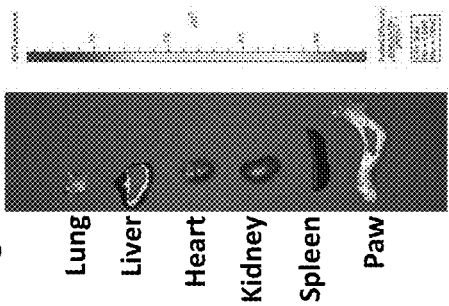
Figure 4D
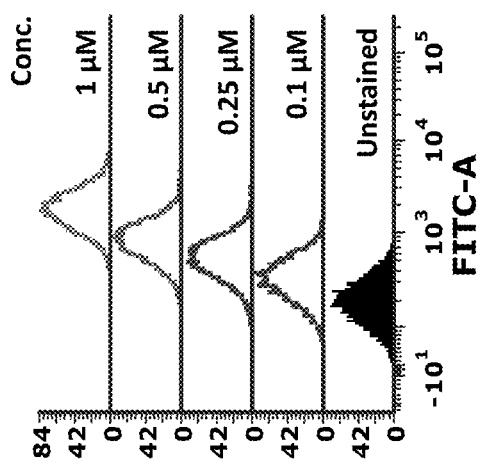
Figure 4A
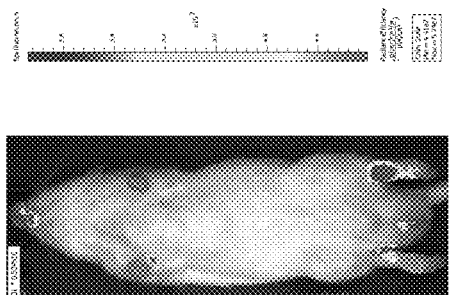
Figure 4C
Figure 4

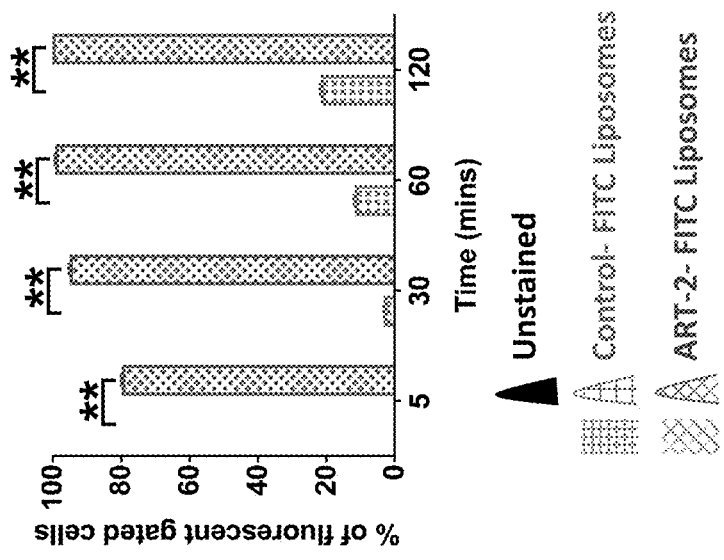
Figure 5D
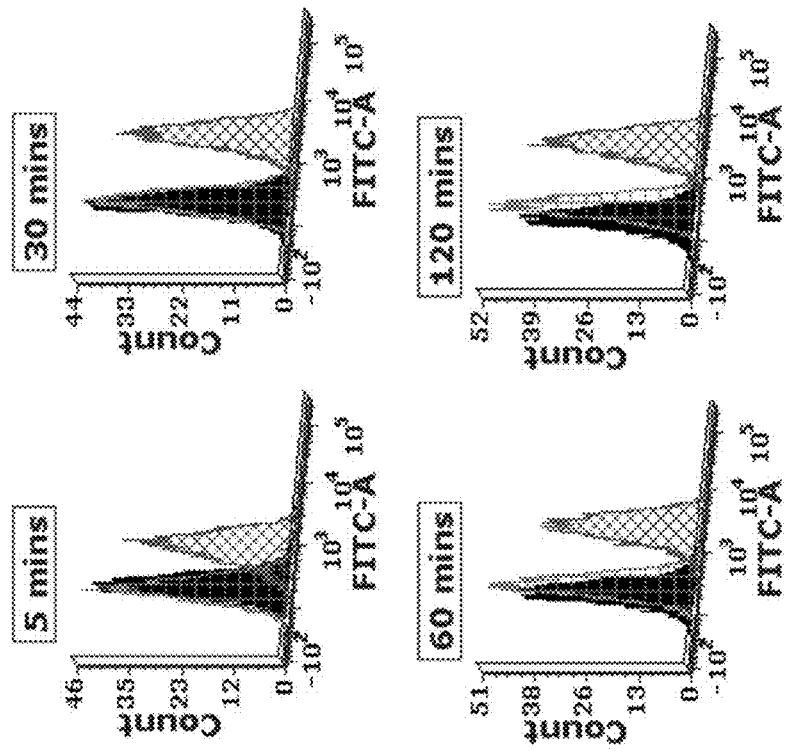
Figure 5C
Figure 5 cont.

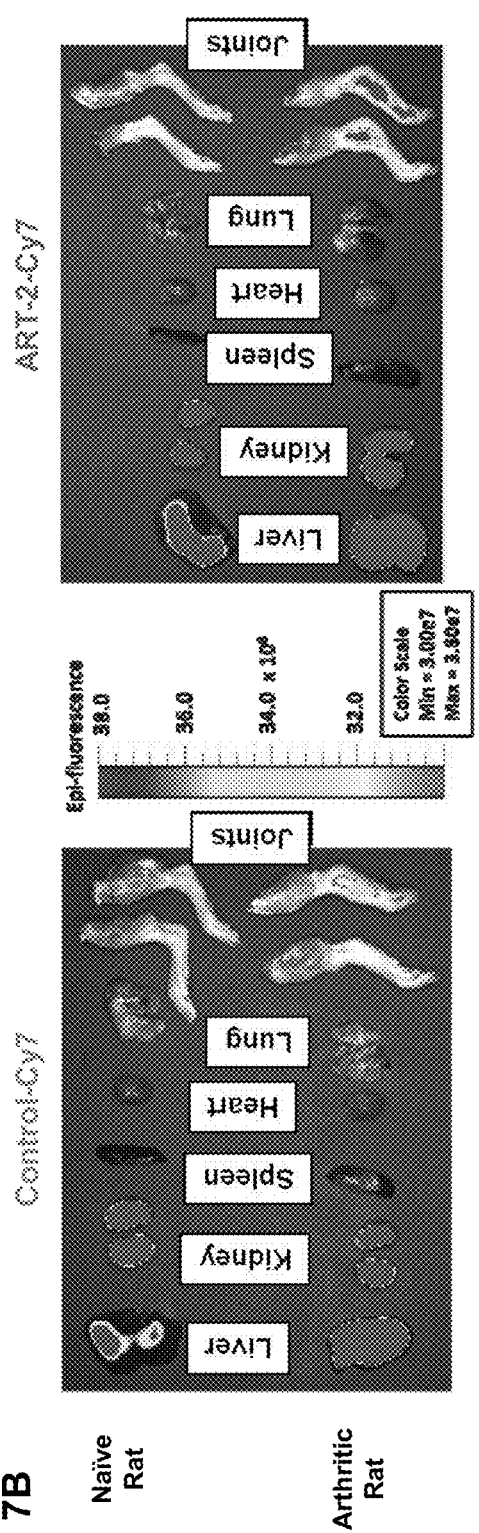
Figure 7B
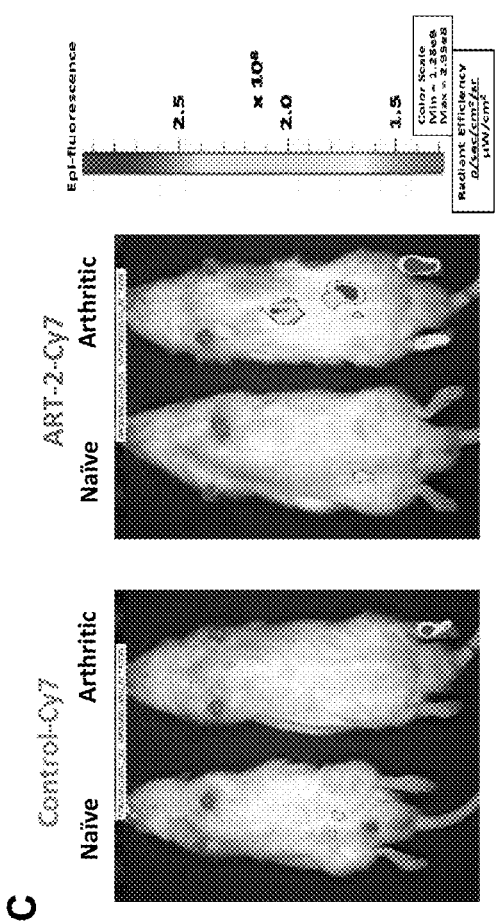
Figure 7C
Figure 7 cont.

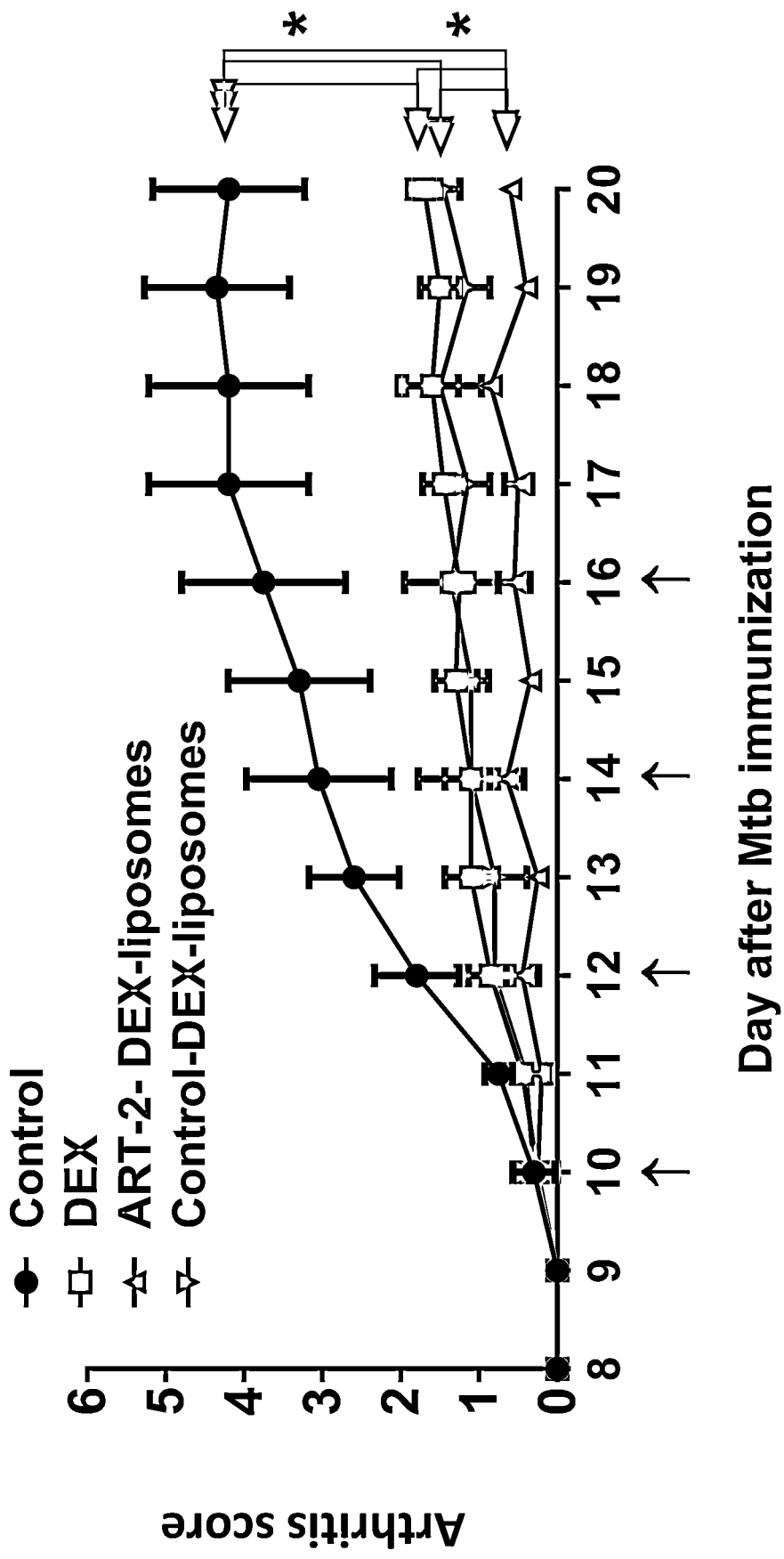

Figure 8B
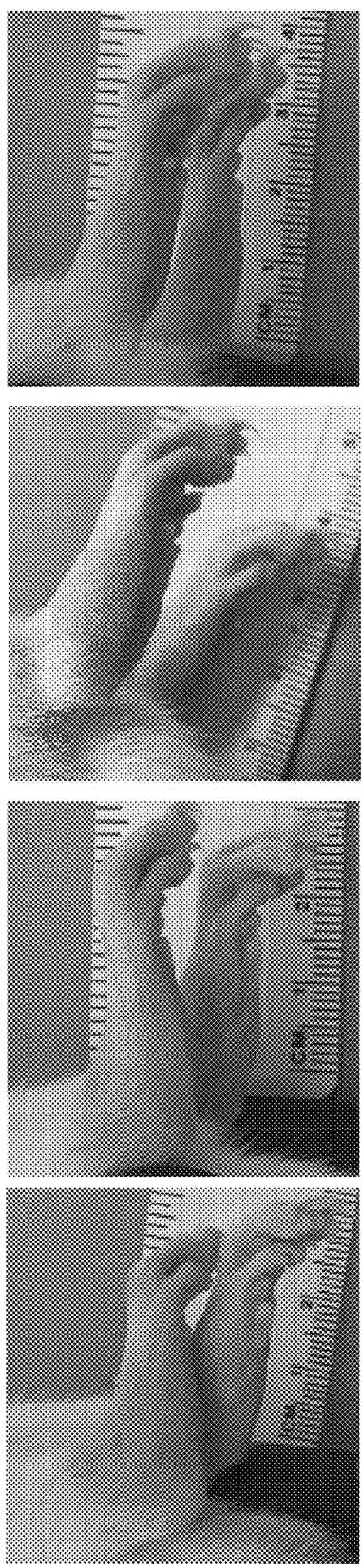
Figure 8C
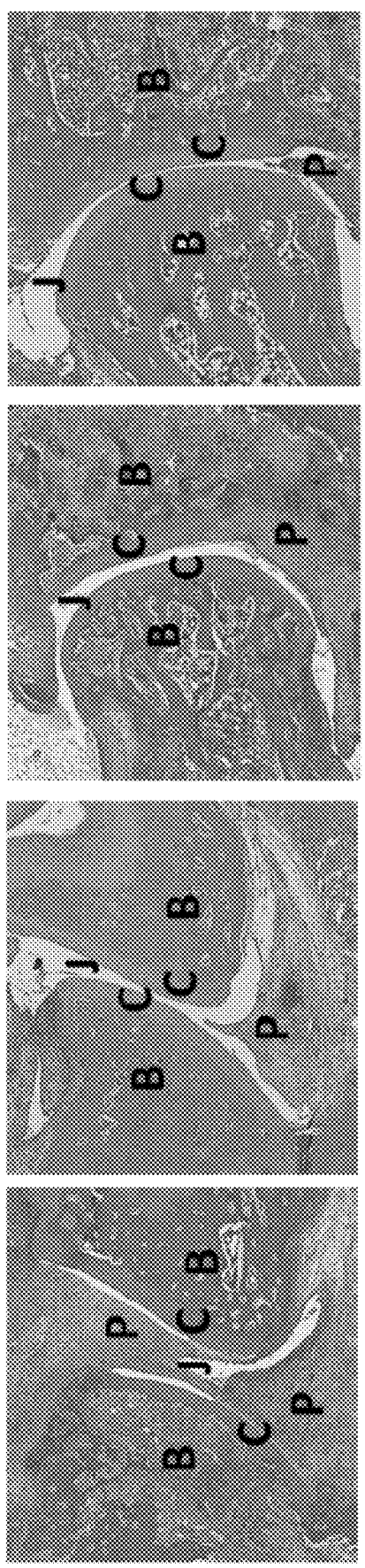
Figure 8 cont.

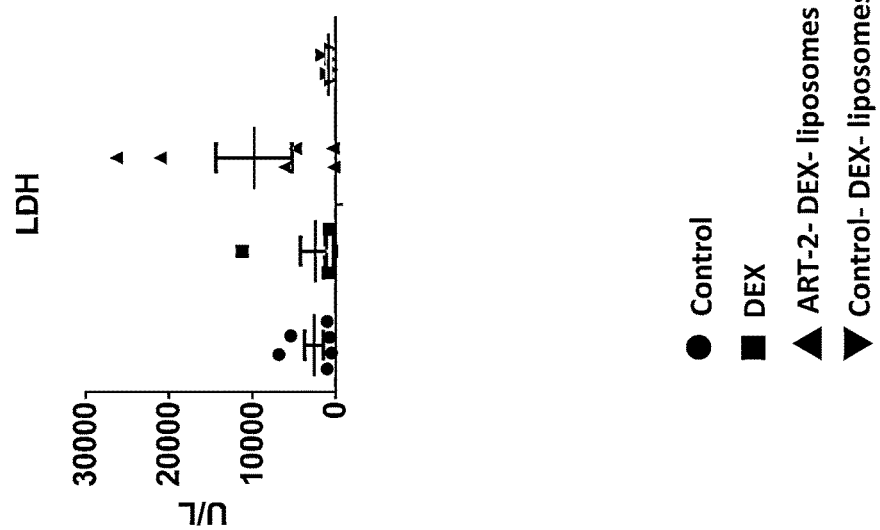
Figure 9D
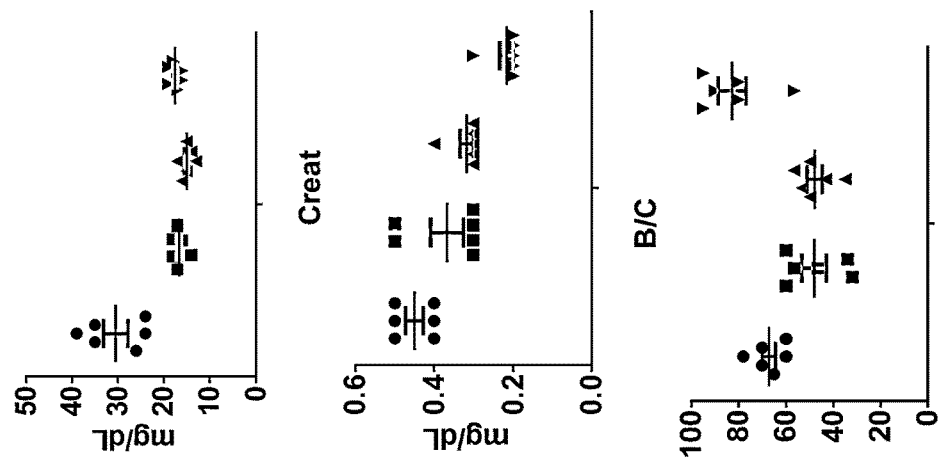
Figure 9C
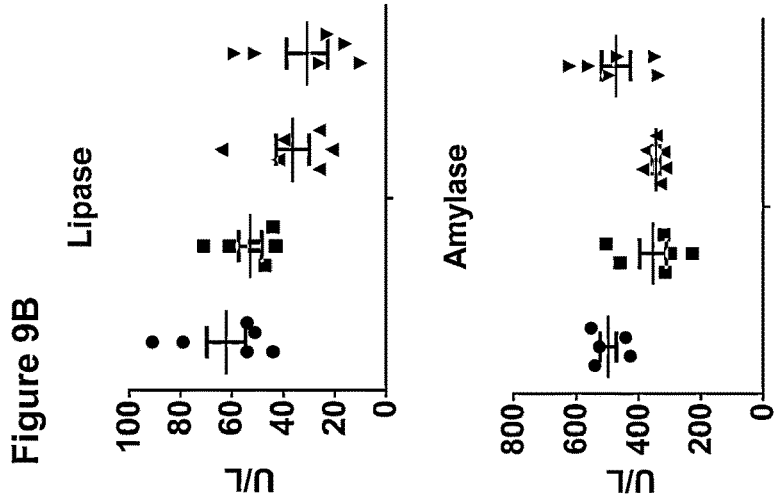
Figure 9B
Figure 9 cont.

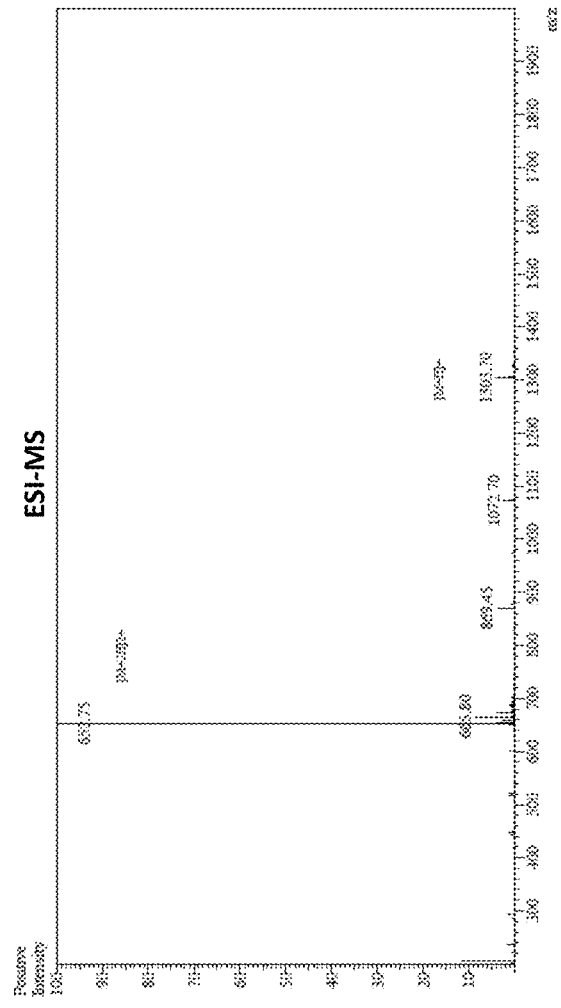
Figure 10A
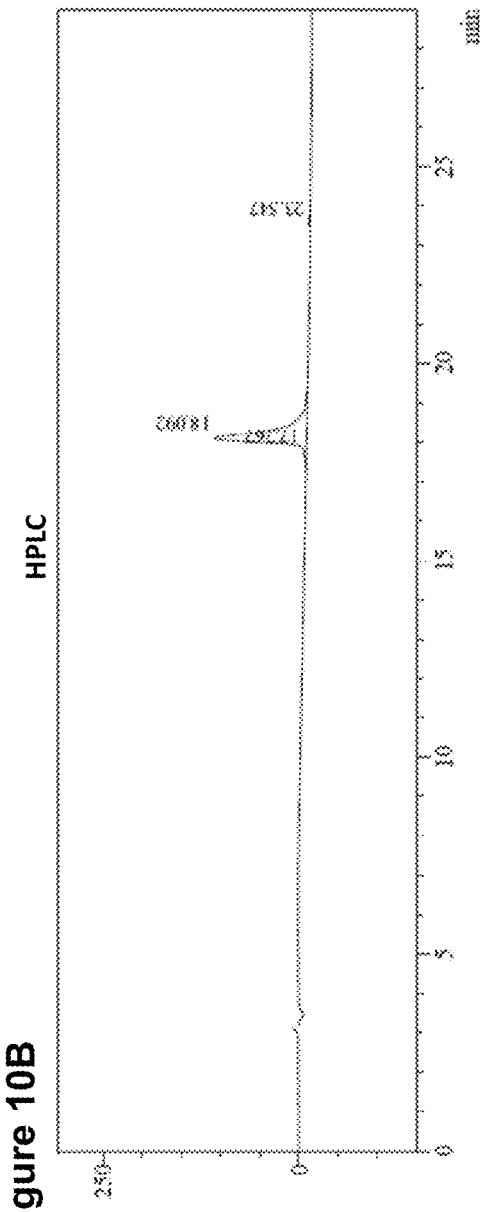
Figure 10B
Figure 10

SEQUENCE LISTING

<160> NUMBER OF SEQ ID NOS: 2

<210> SEQ ID NO 1
<211> LENGTH: 9
<212> TYPE: PRT
<213> ORGANISM: Artificial Sequence
<220> FEATURE:
<223> OTHER INFORMATION: ART-2

<400> SEQUENCE: 1

Cys Lys Pro Phe Asp Arg Ala Leu Cys
1               5

<210> SEQ ID NO 2
<211> LENGTH: 9
<212> TYPE: PRT
<213> ORGANISM: Artificial Sequence
<220> FEATURE:
<223> OTHER INFORMATION: synovial endothelium-targeting peptide

<400> SEQUENCE: 2

Cys Lys Ser Thr His Asp Arg Leu Cys
1               5

PEPTIDE-TARGETED LIPOSOMAL DELIVERY FOR TREATMENT, DIAGNOSIS, AND IMAGING OF DISEASES AND DISORDERS

CROSS-REFERENCE TO RELATED APPLICATIONS

This application claims priority under 35 U.S.C. § 119(e) to U.S. Provisional Patent Application Ser. No. 62/821,750, filed Mar. 21, 2019, the disclosure of which is incorporated herein by reference in its entirety.

STATEMENT REGARDING FEDERALLY SPONSORED RESEARCH OR DEVELOPMENT

This invention was made with government support under Grant Number AT004321 awarded by the National Institutes of Health, and VA Merit Award Number BX002424 awarded by U.S. Department of Veterans Affairs. The government has certain rights in the invention.

REFERENCE TO A "SEQUENCE LISTING," A TABLE, OR A COMPUTER PROGRAM LISTING APPENDIX SUBMITTED AS AN ASCII TEXT FILE

The Sequence Listing written in the ASCII text file named "72GJ-325710-US_Substitute_Sequence_Listing", created on Mar. 29, 2023, 908 bytes, to add SEQ ID NO: 2 that was missing in ASCII text file named, "206187_0014_00US_SequenceListing_corrected_ST25.txt", created on Sep. 16, 2022, 700 bytes, is hereby incorporated by reference in its entirety.

BACKGROUND OF THE INVENTION

Rheumatoid arthritis (RA) is a debilitating autoimmune disease involving chronic inflammation of the joints, which ultimately results in joint damage and deformity. This can impose a heavy socioeconomic burden on the society (Firestein G S, 2003, Nature 423:356-361; Harris E D, 1990, N Engl J Med 322:1277-1289). Non-steroid anti-inflammatory drugs (NSAIDs) and disease-modifying anti-rheumatic drugs (DMARDs), including biologics (e.g., anti-tumor necrosis factor-α (TNF-α) and anti-interleukin-6 receptor (IL-6R) antibodies) represent the mainstream anti-arthritic drugs currently in use for RA therapy (Gibofsky A, 2014, Am J Manag Care 20:S136-144; Curtis J R et al., 2011, Clin Ther 33:679-707; Kim G W et al., 2015, Arch Pharm Res 38:575-584; Bui V L et al., 2018, Clinical Immunology 2018; Sfikakis P P et al., 2011, Clinical Immunology 141: 231-235). These are potent drugs, but their long-term use may lead to severe adverse reactions, such as infections in the case of biologics (Sfikakis P P et al., 2011, Clinical Immunology 141:231-235; Ramiro S et al., 2017, Annals of the Rheumatic Diseases 76:1101-1136). The above-mentioned drugs are administered to patients either orally or by subcutaneous/intramuscular injections, and thereby these drugs are distributed widely to several tissues in the body besides the diseased site, i.e., the inflamed joints. This results in exposure of many healthy organs of the body to those drugs that are intended for the inflamed joints. For this reason, prolonged arthritis therapy is frequently associated with damage to organs, such as the liver and kidney.

For instance, dexamethasone (DEX) is a glucocorticoid, which has anti-inflammatory and immunosuppressive properties, and is used in the clinic for the treatment of RA and other immune-mediated diseases, including allergies (Bordag N et al., 2015, Scientific Reports 5:15954). The effects of a glucocorticoid are mediated upon its binding to a specific receptor in the cytoplasm, following which the complex is transported into the nucleus, where it causes trans-repression of various genes involved in the inflammatory processes. Nuclear factor-kappa B (NF-kB) and activator protein (AP-1) are representative transcription factors inhibited in this process. Prolonged use of high dose of DEX can cause a variety of adverse effects involving the gastrointestinal system (e.g., gastritis); cardiovascular system (e.g., hypertension); musculoskeletal system (e.g., osteoporosis and muscle weakness); and metabolic disease (e.g., diabetes) (Bordag N et al., 2015, Scientific Reports 5:15954). Mechanisms of action of DEX in attenuating arthritic inflammation include suppression of a variety of mediators of inflammation such as cytokines, chemokines, and adhesion molecules, which in turn lead to inhibition of leukocyte infiltration into the site of inflammation (Tsurufuji S et al., 1984, The Journal of Pharmacology and Experimental Therapeutics 229:237-243). Also reported is DEX-induced suppression of fibroblast activation by activated memory T cells (Dankers W et al., 2018, Arthritis Research & Therapy 20:212). Thus, there is a need for targeting the drugs to the diseased joints in RA to enhance their efficacy in controlling arthritis.

Targeted drug delivery is a rapidly emerging area of biotechnology. Most of the effort in this regard has been invested in the treatment of cancer. In comparison, there are relatively fewer studies for the application of nanotechnology to the treatment of autoimmune diseases, such as RA. Nanoparticles of diverse types (e.g., liposomes, micelles, dendrimers, etc.) (Allen T M et al., 2013, Advanced Drug Delivery Reviews 65:36-48; Koning G A et al, 2006, Arthritis and Rheumatism 54:1198-1208; Ruoslahti E. et al., 2010, The Journal of Cell Biology 188:759-768; Sercombe L et al., 2015, Frontiers in Pharmacology 6:286; Yang M et al., 2017, Journal of Controlled Release 252:108-124) and conjugates of a drug with a polymer or folate (Yang M et al., 2017, Journal of Controlled Release 252:108-124; Ferrari M et al., 2015, Nature Reviews 11:328-337; Qi R et al., 2015, Journal of Biomedical Nanotechnology 11:1431-1441; Yang M et al., 2018, Nanomedicine: Nanotechnology, Biology and Medicine 14:1815-1816) are being developed and tested for this purpose in different diseases, including RA. Liposomes are well-optimized nanoparticles for drug delivery (Allen T M et al., 2013, Advanced Drug Delivery Reviews 65:36-48; Sercombe L et al., 2015, Frontiers in Pharmacology 6:286). While a large proportion of studies on liposomes used plain liposomes encapsulating a therapeutic agent, studies in tumor therapy by Ruoslahti and colleagues (Ruoslahti E et al., 2010, The Journal of Cell Biology 188:759-768; Ruoslahti E, 2012, Advanced Materials 24:3747-3756; Teesalu T et al., 2013, Frontiers in Oncology 3:216) and other investigators (Perez-Herrero E et al., 2015, European Journal of Pharmaceutics and Biopharmaceutics 93:52-79; Zhao G et al., 2013, International Journal of Nanomedicine 8:61-71) have used peptide ligands to direct liposomes to specific tumors/tissues. Subsequently, similar ligand-targeted nanoparticle therapy approaches are also being developed for RA (Koning G A et al., 2006, Arthritis and Rheumatism 54:1198-1208; Vanniasinghe A S et al., 2014, Clinical Immunology 151:43-54; Poh S et al., 2017, Nanomedicine 12:2441-2451; Nogueira E et al., 2015, Journal of Biomedical Nanotechnology 11:2243-2252), systemic lupus erythematosus (SLE) (Look M et al., 2013, The Journal of Clinical Investigation 123:1741-1749), and other autoimmune diseases, demonstrating that novel ways to improve the benefit/risk ratio (or therapeutic index) of various drugs are being sought.

Thus, there is a need in the art for an agent-vehicle, such as a ligand, that can carry therapeutic agents, diagnostic agents, imaging agents, or any combination thereof to disease effected sites, such as arthritic joints, and therefore target the agents to the diseased sites in order to enhance the agent's efficacy in treating, diagnosing, or imaging said diseases. The present invention addresses this unmet need in the art.

SUMMARY OF THE INVENTION

The present invention relates to a peptide comprising an amino acid sequence of CKPFDRALC (SEQ ID NO: 1) as a novel tissue-targeting peptide. The present invention also includes methods of using peptide-targeted agent delivery using the tissue-targeting peptide to improve the effectiveness of the agent in inhibiting, diagnosing, or imaging a disease or disorder as compared with delivery of the untargeted agent, while diminishing off-target adverse effects.

In one aspect, the invention is related to compositions comprising at least one peptide. In one embodiment, the peptide comprises an amino acid sequence of CKPFDRALC (SEQ ID NO: 1). In one embodiment, the peptide is a tissue-targeting peptide selectively targeting a biological tissue.

In various aspects of the invention, the peptide is conjugated to at least one agent, liposome, lipid, pharmaceutically acceptable carrier, or any combination thereof.

In various embodiments, the targeted biological tissue is a connective tissue, joint tissue, synovial tissue, vascular tissue, neovascular tissue, muscle tissue, nervous tissue, epithelial tissue, endothelial cells and/or endothelial tissue, tumor tissue, or any combination thereof. In various embodiments, the connective tissue is a fibrous connective tissue, skeletal connective tissue, fluid connective tissue, or any combination thereof. In various embodiments, the biological tissue is blood, bone, tendon, ligament, adipose, areolar tissues, or any combination thereof. In various embodiments, the muscle tissue is a visceral (smooth) muscle tissue, skeletal muscle tissue, cardiac muscle tissue, or any combination thereof. In various embodiments, the nervous tissue is a brain tissue, spinal cord tissue, or any combination thereof. In various embodiments, the epithelial tissue is a simple squamous epithelium, stratified squamous epithelium, simple cuboidal epithelium, transitional epithelium, pseudostratified columnar epithelium, columnar epithelium, glandular epithelium, ciliated columnar epithelium, or any combination thereof. In various embodiments, the epithelial tissue is a skin tissue, airway tissue, reproductive tract tissue, digestive tract tissue, or any combination thereof. The endothelial tissue can be vascular tissue, particularly neovascular tissue, such as neovascular tissue associated with disease or inflammatory conditions. Examples of neovascular tissue associated with disease that can be targeted by the peptide of the invention includes (but is not necessarily limited to) neovascular tissue associated with autoimmune and/or inflammatory diseases/conditions such as arthritis (for example, rheumatoid arthritis), neovascularizing ocular diseases (e.g., macular degeneration and diabetic retinopathy), and cancer.

In various aspects of the invention, the composition further comprises at least one agent, liposome, lipid, pharmaceutically acceptable carrier, or any combination thereof.

In various embodiments, the agent is a protein, peptide, peptidomimetic, antibody, ribozyme, vector, nucleic acid molecule, antisense nucleic acid, small molecule drug, organic compound, inorganic compound, or any combination thereof.

In various embodiments, the agent is a therapeutic agent, prophylactic agent, diagnostic agent, imaging agent, contrast agent, microparticle, nanoparticle, or any combination thereof. In various embodiments, the therapeutic agent is glucocorticoid, biologic, anti-arthritis drug, or any combination thereof. In various embodiments, the glucocorticoid is cortisol (hydrocortisone), cortisone, prednisone, prednisolone, methylprednisolone, dexamethasone, betamethasone, triamcinolone, fludrocortisone acetate, deoxycorticosterone acetate, or any combination thereof. In various embodiments, the contrast agent is a radiocontrast medium, iodinated contrast agent, iodine, ipodate sodium, diatrizoate, metrizoate, iothalamate, ioxaglate, iopamidol, iohexol, ioxilan, iopromide, iodixanol, ioversol, barium, MRI contrast agent, gadolinium, ultrasound contrast agent, saline solution, or any combination thereof.

The present invention also includes methods of delivering an agent to a biological tissue. In various aspects of the invention, the methods comprise administering a composition to a subject in need thereof. In one embodiment, the composition comprises an agent and at least one targeting peptide, such as a peptide comprising the amino acid sequence of SEQ ID NO: 1. In various embodiments, the peptide is conjugated to at least one agent, liposome, lipid, pharmaceutically acceptable carrier, or any combination thereof. In various embodiments, the agent is a therapeutic agent, prophylactic agent, diagnostic agent, imaging agent, contrast agent, microparticle, nanoparticle, or any combination thereof.

The present invention also includes methods of treating a disease or disorder in a subject by administration of an agent that is targeted to a biological tissue of a subject. In one embodiment, the method comprises administering the composition of the invention to a subject in need thereof. In various embodiments, the composition comprises at least one targeting peptide and at least one agent, liposome, lipid, pharmaceutically acceptable carrier, or any combination thereof. In one embodiment, the targeting peptide comprises an amino acid sequence of CKPFDRALC (SEQ ID NO: 1). In various embodiments, the peptide is conjugated to at least one agent, liposome, lipid, pharmaceutically acceptable carrier, or any combination thereof.

In various embodiments, the agent is a protein, peptide, peptidomimetic, antibody, ribozyme, vector, nucleic acid molecule, antisense nucleic acid, small molecule drug, organic compound, inorganic compound, or any combination thereof. In various embodiments, the agent is a therapeutic agent, prophylactic agent, diagnostic agent, imaging agent, contrast agent, microparticle, nanoparticle, or any combination thereof. In one embodiment, the therapeutic agent is a glucocorticoid, biologic, anti-arthritis drug, or any combination thereof. In various embodiments, the glucocorticoid is cortisol (hydrocortisone), cortisone, prednisone, prednisolone, methylprednisolone, dexamethasone, betamethasone, triamcinolone, fludrocortisone acetate, deoxycorticosterone acetate, or any combination thereof.

In various embodiments, the disease or disorder is an immune-mediated disease, autoimmune disease, inflammatory disease, autoinflammatory disease, cancer, or any combination thereof. In various embodiments, the disease or disorder is an acne vulgaris, allergy, asthma, atherosclerosis, celiac disease, chronic prostatitis, colitis, diabetes mellitus type 1, diverticulitis, Graves' disease, glomerulonephritis, hidradenitis suppurativa, hypersensitivity, inflammatory bowel disease, interstitial cystitis, leukocyte defects, lichen planus, mast cell activation syndrome, mastocytosis, multiple sclerosis, myopathies, otitis, pelvic inflammatory disease, psoriasis, reperfusion injury, rheumatic fever, rheumatoid arthritis, osteoarthritis, spondyloarthropathy, rhinitis, sarcoidosis, systemic lupus erythematosus, transplant rejection, vasculitis, age-related macular degeneration, diabetic retinopathy, or any combination thereof.

In one aspect, the invention also includes methods of diagnosing a disease or disorder in a subject by delivery of an agent to a biological tissue of a subject. In one embodiment, the method comprises administering the composition of the invention to a subject in need thereof. In various embodiments, the composition comprises at least one targeting peptide and at least one agent, liposome, lipid, pharmaceutically acceptable carrier, or any combination thereof. In one embodiment, the peptide comprises an amino acid sequence of CKPFDRALC (SEQ ID NO: 1).

In another aspect, the invention includes methods of imaging a disease or disorder in a subject by administering an agent that is targeted to a biological tissue of a subject. In one embodiment, the method comprises administering a composition to a subject in need thereof. In various embodiments, the composition comprises at least one targeting peptide and at least one agent, liposome, lipid, pharmaceutically acceptable carrier, or any combination thereof. In one embodiment, the targeting peptide comprises an amino acid sequence of CKPFDRALC (SEQ ID NO: 1).

The present invention also includes a composition comprising an isolated nucleic acid molecule encoding a tissue-targeting peptide. In one aspect of the invention, the isolated nucleic acid molecule encodes a tissue-targeting peptide comprising an amino acid sequence of CKPFDRALC (SEQ ID NO: 1).

The present invention also includes a composition for targeted delivery of an agent. In one aspect, the composition comprises at least one peptide conjugated to a therapeutically effective amount of at least one agent, liposome, lipid, pharmaceutically acceptable carrier, or any combination thereof. In one embodiment, the peptide is a tissue-targeting peptide comprising an amino acid sequence of CKPFDRALC (SEQ ID NO: 1).

BRIEF DESCRIPTION OF THE DRAWINGS

The following detailed description of various embodiments of the invention will be better understood when read in conjunction with the appended drawings. For the purpose of illustrating the invention, these are shown in the drawings illustrative embodiments. It should be understood, however, that the invention is not limited to the precise arrangements and instrumentalities of the embodiments shown in the drawings.

FIG. 1, comprising FIG. 1A and FIG. 1B, the chemical structure of ART-2 and ART-2-lipopeptide. FIG. 1A depicts the chemical structure of ART-2-peptide (CKPFDRALC (SEQ ID NO: 1)). FIG. 1B depicts the ART-2-lipopeptide structure.

FIG. 2A through FIG. 2F, depicts the characteristics and stability of various liposomes. FIG. 2A depicts the size of ART-2-DEX-liposomes. FIG. 2B depicts the size of the control, DEX-liposomes. FIG. 2C depicts the stability results of these two types of liposomes stored at room temperature that were tested on d 0 and d 14 for their size. FIG. 2D depicts the stability results of these two types of liposomes stored at room temperature that were tested on d 0 and d 14 for their polydispersity index (PDI). FIG. 2E depicts the stability results of ART-2-FITC-liposomes and control FITC-liposomes stored at room temperature that were tested on d 0 and d 14 for their size. FIG. 2F depicts the stability results of these two types of FITC-containing liposomes stored at room temperature that were tested on d 0 and d 14 for their polydispersity index (PDI).

FIG. 3, comprising FIG. 3A through FIG. 3D, depicts the TEM images and Zeta potential of liposomes. FIG. 3A depicts the TEM image of DEX-containing ART-2-liposomes. FIG. 3B depicts the TEM image of the control, DEX-containing liposomes. FIG. 3C depicts the Zeta potential of DEX-containing ART-2-liposomes. FIG. 3D depicts the Zeta potential of the control, DEX-containing liposomes.

FIG. 4, comprising FIG. 4A through FIG. 4D, depicts in vitro and in vivo binding of ART-2 peptides. FIG. 4A depicts the binding of fluorescein isothiocyanate (FITC)-labeled ART-2 peptide to human umbilical vein endothelial cells (HUVEC) in vitro (HUVEC were treated with ART-2-FITC peptides for 2 h at the indicated concentrations). A representative histogram is shown. FIG. 4B depicts HUVEC that were stained with ART-2-FITC peptide at 0.5 µM concentration, PE-labeled CD31 (a marker for endothelial cells), and DAPI (for nucleus staining) and examined under a fluorescence microscope. FIG. 4C depicts in vivo distribution of Cyanine 7 (Cy7)-labeled ART-2 peptide: real-time fluorescence imaging of arthritic rats at 4 h time point after i.v. injection of the peptide following the procedure described in the legend to FIG. 7. FIG. 4D depicts images of ex-vivo fluorescence of different organs harvested from arthritic rats at 4 h after i.v. injection of ART-2-Cy7-peptide.

FIG. 5A through FIG. 5D, depicts endothelial cell-binding of liposomes in vitro. For each set, the fluorescence intensity is shown as a histogram as well as a graph. FIG. 5A depicts flow cytometry results in a graph form for HUVEC that were treated with ART-2-FITC liposomes or control-FITC liposomes for 2 h at the indicated concentrations. FIG. 5B depicts flow cytometry results in a histogram form for HUVEC that were treated with ART-2-FITC liposomes or control-FITC liposomes for 2 h at the indicated concentrations. FIG. 5C depicts flow cytometry results in a graph form for HUVEC that were treated with ART-2-FITC liposomes or control-FITC liposomes for different duration of time at one concentration (0.5 µM). FIG. 5D depicts flow cytometry results in a histogram form for HUVEC that were treated with ART-2-FITC liposomes or control-FITC liposomes for different duration of time at one concentration (0.5 µM).

FIG. 6A through FIG. 6D, depicts cytotoxicity results of ART-2- and Control liposomes that were tested using HUVEC exposed to different concentrations of liposomes (0.1 µM-10 µM) for the indicated period of time (4 h-48 h). The results are presented as a mean±SEM (n=3). FIG. 6A depicts cytotoxicity results of ART-2- and Control liposomes that were tested using HUVEC exposed to different concentrations of liposomes (0.1 µM-10 µM) for 4 h. FIG. 6B depicts cytotoxicity results of ART-2- and Control liposomes that were tested using HUVEC exposed to different concentrations of liposomes (0.1 M-10 µM) for 12 h. FIG. 6C depicts cytotoxicity results of ART-2- and Control liposomes that were tested using HUVEC exposed to different concentrations of liposomes (0.1 µM-10 µM) for 24 h. FIG. 6D depicts cytotoxicity results of ART-2- and Control liposomes that were tested using HUVEC exposed to different concentrations of liposomes (0.1 µM-10 µM) for 48 h.

FIG. 7, comprising FIG. 7A through FIG. 7C, depicts in vivo imaging of systemically-administered liposomes. FIG. 7A depicts imaging results of ART-2-displaying or control liposomes containing Cy7 within them that were injected intravenously into arthritic rats and their distribution in the body was assessed by NIRF-imaging at periodic intervals spanning from 5 min to 6 h. FIG. 7B depicts imaging results of various organs (indicated in the figure) that were harvested after 6 h of injection of Cy-7-containing liposomes into arthritic or naïve rats. Ex-vivo imaging was performed using the same equipment as that used for in vivo imaging above. FIG. 7C depicts in vivo imaging of arthritic and naïve rats after injection of Cy-7-containing liposomes as indicated in the figure.

FIG. 8, comprising FIG. 8A through FIG. 8C, depicts comparative efficacy of liposomal DEX and free DEX for arthritis therapy. Arthritis was induced in Lewis rats by s.c. injection of heat-killed *Mycobacterium tuberculosis* H37Ra (Mtb). At the time of appearance of signs of arthritis (disease onset), rats were randomized (n=5/group) and given intravenously 4 injections every two days starting from d 10 (indicated by arrows) of the following preparations: ART-2-DEX liposomes, control-DEX liposomes, or free DEX. Another arthritic group given only PBS (vehicle) served as a reference group of rats for comparison with other groups. All groups received the same dose of DEX, namely 0.1 mg/Kg. FIG. 8A depicts disease severity as indicated by arthritic scores (mean±SD), and P<0.05 indicates statistically significance. FIG. 8B depicts representative hind paw (photographs). FIG. 8C depicts histological features of hind paws (bone: B; cartilage: C; joint space: J; and pannus: P).

FIG. 9A through FIG. 9D, depicts results of serum testing for the relative adverse effects of DEX in different treatment groups. Sera were collected from rats (n=6/group) treated with DEX delivered via ART-2-displaying liposomes, Control-liposomes, or as free drug. Serum collection time was d 20 after Mtb injection. FIG. 9A depicts results of sera that were tested for the indicated enzymes or other analytes to assess liver and biliary system toxicity. FIG. 9B depicts results of sera that were tested for the indicated enzymes or other analytes to assess pancreatic toxicity. FIG. 9C depicts results of sera that were tested for the indicated enzymes or other analytes to assess kidney toxicity. FIG. 9D depicts results of sera that were tested for the indicated enzymes or other analytes to assess acute/chronic tissue damage.

FIG. 10, comprising FIG. 10A and FIG. 10B, depicts ESI-MS and HPLC results of ART-2-lipopeptide. FIG. 10A depicts ESI-MS spectrum of ART-2-lipopeptide: m/z calculated 1303.76 for CKPFDRALC (SEQ ID NO: 1)-NH—$C_{18}H_{37}$, observed 1303.7 ([M+H]+) and 652.75 ([M+2H] 2+). FIG. 10B depicts HPLC chromatogram of ART-2-lipopeptide.

DETAILED DESCRIPTION

Figure 2:
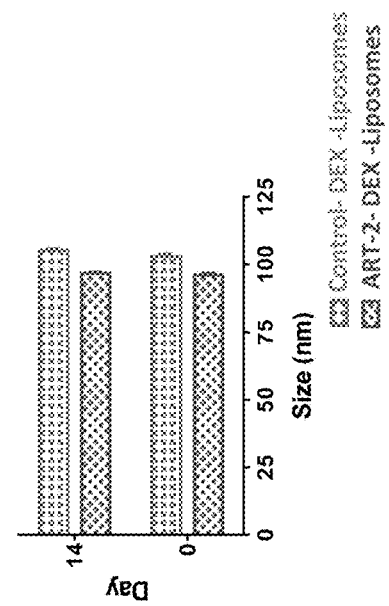
FIG. 2, comprising
Figure 2:
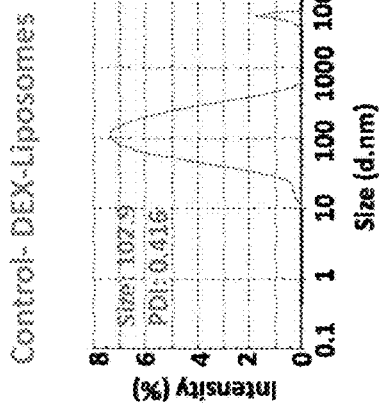
Figure 2:
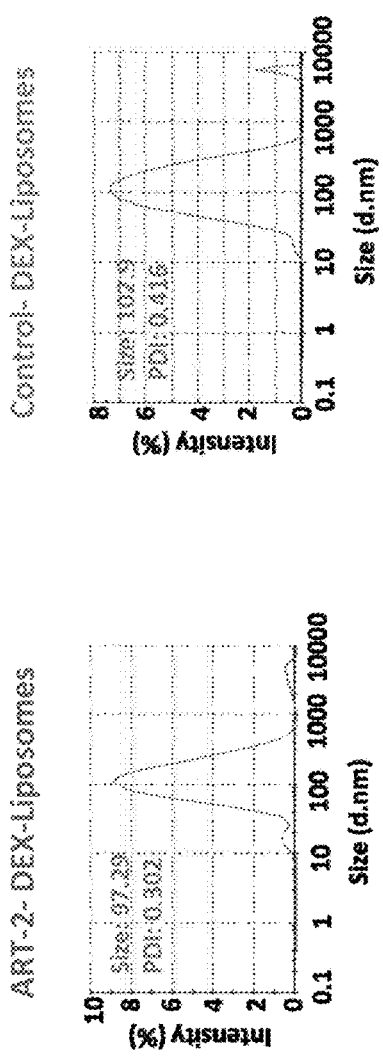
Figure 2:
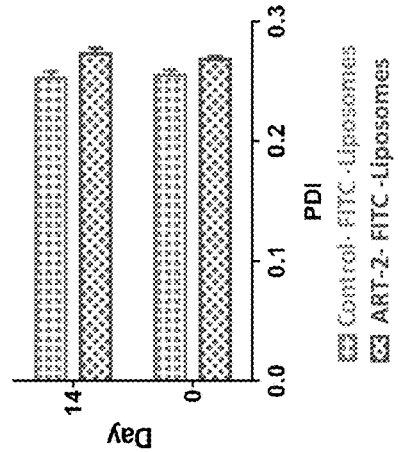
Figure 2:
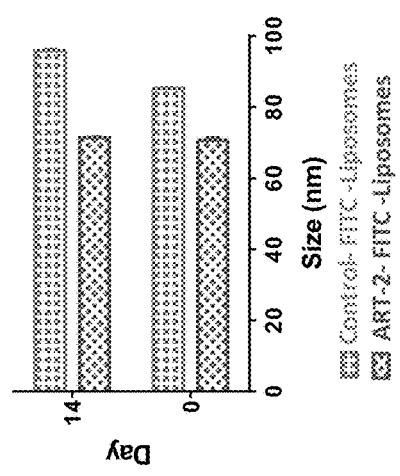
Figure 2:
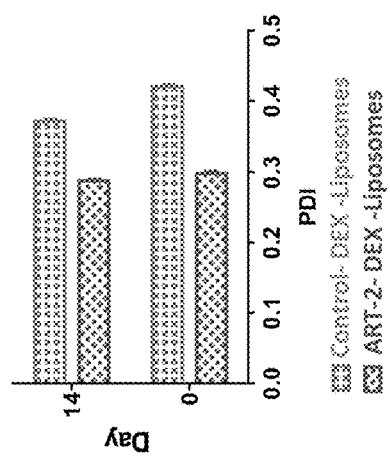

The present invention relates in part to a peptide-targeted agent delivery system that helps improve the therapeutic index of a known therapeutic agents, such as anti-arthritic drugs, by enhancing efficacy compared to free drug, while diminishing off-target adverse effects. The methodology of the present invention can be adapted for targeted delivery of an agent for the treatments of a variety of diseases and disorders. Furthermore, the peptide-targeted agent delivery system can be used to deliver one or more therapeutic agents, imaging agents, diagnosing agents in the same agent-delivery vehicle. The peptide-targeted agent delivery system can be also used for delivering one or more imaging agents, diagnostic agents, and therapeutic agents either in the same agent-delivery vehicle or concurrently or serially in two or more separate agent-delivery vehicles.

Definitions

Unless defined otherwise, all technical and scientific terms used herein have the same meaning as commonly understood by one of ordinary skill in the art to which this invention belongs. Any methods and materials similar or equivalent to those described herein can be used in the practice or testing of the present invention.

As used herein, each of the following terms has the meaning associated with it in this section.

The articles "a" and "an" are used herein to refer to one or to more than one (i.e., to at least one) of the grammatical objects of the article. By way of example, "an element" means one element or more than one element.

"About" as used herein when referring to a measurable value such as an amount, a temporal duration, and the like, is meant to encompass variations of ±20% or ±10%, or ±5%, or ±1%, or ±0.1% from the specified value; as such variations are appropriate to perform the disclosed methods.

The term "biological tissue" as used herein refers to a collection of interconnected cells and extracellular matrix that perform a similar function or functions within an organism. Biological tissues include, without limitation, connective tissue, joint tissue, synovial tissue, muscle tissue, nervous tissue (of the brain, spinal cord, and nerves), epithelial tissue, endothelial tissue, tumor tissue, and organ tissue. Connective tissue includes fibrous tissue like fascia, tendon, ligaments, heart valves, bone, and cartilage. Muscle tissue includes skeletal muscle tissue, smooth muscle tissue, such as esophageal, stomach, intestinal, bronchial, uterine, urethral, bladder, and blood vessel tissue, and cardiac muscle tissue. Epithelial tissue includes simple epithelial tissue, such as alveolar epithelial tissue, blood vessel endothelial tissue, and heart mesothelial tissue, and stratified epithelial tissue. "Biological tissue" includes structures such as joints and synovial tissue and can include neovascularized tissue such as that resulting from inflammatory or other disease states including but not limited to arthritis, retinopathies such as macular degeneration and diabetic retinopathy, and cancer, as will be understood by the skilled artisan.

The terms "cells" and "population of cells" are used interchangeably and refer to a plurality of cells, i.e., more than one cell. The population may be a pure population comprising one cell type. Alternatively, the population may comprise more than one cell type. In the present invention, there is no limit on the number of cell types that a cell population may comprise.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, the term "analog," "analogue," or "derivative" is meant to refer to a chemical compound or molecule made from a parent compound or molecule by one or more chemical reactions. As such, an analog can be a structure having a structure similar to that of the small molecule therapeutic agents described herein or can be based on a scaffold of a small molecule therapeutic agents described herein, but differing from it in respect to certain components or structural makeup, which may have a similar or opposite action metabolically. An analog or derivative of any of a small molecule inhibitor in accordance with the present invention can be used to treat a disease or disorder.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

By the term "specifically bind" or "specifically binds," as used herein, is meant that a first molecule (e.g., an antibody) preferentially binds to a second molecule (e.g., a particular antigenic epitope), but does not necessarily bind only to that second molecule. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross-reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

A "nucleic acid" refers to a polynucleotide and includes poly-ribonucleotides and poly-deoxyribonucleotides. Nucleic acids according to the present invention may include any polymer or oligomer of pyrimidine and purine bases, preferably cytosine, thymine, and uracil, and adenine and guanine, respectively. (See Albert L. Lehninger, Principles of Biochemistry, at 793-800 (Worth Pub. 1982), which is herein incorporated in its entirety for all purposes). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

An "oligonucleotide" or "polynucleotide" is a nucleic acid ranging from at least 2, preferably at least 8, 15 or 25 nucleotides in length, but may be up to 50, 100, 1000, or 5000 nucleotides long or a compound that specifically hybridizes to a polynucleotide. Polynucleotides include sequences of deoxyribonucleic acid (DNA) or ribonucleic acid (RNA) or mimetics thereof which may be isolated from natural sources, recombinantly produced or artificially synthesized. A further example of a polynucleotide of the present invention may be a peptide nucleic acid (PNA). (See U.S. Pat. No. 6,156,501 which is hereby incorporated by reference in its entirety.) The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this disclosure. It will be understood that when a nucleotide sequence is represented herein by a DNA sequence (e.g., A, T, G, and C), this also includes the corresponding RNA sequence (e.g., A, U, G, C) in which "U" replaces "T".

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, the term "polymer" refers to a molecule composed of repeating structural units typically connected by covalent chemical bonds. The term "polymer" is also meant to include the terms copolymer and oligomers. In one embodiment, a polymer comprises a backbone (i.e., the chemical connectivity that defines the central chain of the polymer, including chemical linkages among the various polymerized monomeric units) and a side chain (i.e., the chemical connectivity that extends away from the backbone).

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

As used herein, the term "fragment," as applied to a nucleic acid, refers to a subsequence of a larger nucleic acid. As used herein, the term "fragment," as applied to a protein or peptide, refers to a subsequence of a larger protein or peptide.

The term "functionally equivalent" as used herein refers to a polypeptide according to the invention that preferably retains at least one biological function or activity of the specific amino acid sequence of either the first or second peptide.

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double-stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

The term "label" when used herein refers to a detectable compound or composition that is conjugated directly or indirectly to a molecule to generate a "labeled" molecule. The label may be detectable by itself (e.g. radioisotope labels or fluorescent labels) or, in the case of an enzymatic label, may catalyze chemical alteration of a substrate compound or composition that is detectable (e.g., avidin-biotin).

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of at least one sign or symptom of the disease or disorder, the frequency with which at least one sign or symptom is experienced by a patient, or both, is reduced.

The term "cancer" as used herein, refers to the abnormal growth or division of cells. Generally, the growth and/or life span of a cancer cell exceeds, and is not coordinated with, that of the normal cells and tissues around it. Cancers may be benign, pre-malignant or malignant. Cancer occurs in a variety of cells and tissues, including, but not limited to, the oral cavity (e.g., mouth, tongue, pharynx, etc.), digestive system (e.g., esophagus, stomach, small intestine, colon, rectum, liver, bile duct, gall bladder, pancreas, etc.), respiratory system (e.g., larynx, lung, bronchus, etc.), bones, joints, skin (e.g., basal cell, squamous cell, meningioma, etc.), breast, genital system, (e.g., uterus, ovary, prostate, testis, etc.), urinary system (e.g., bladder, kidney, ureter, etc.), eye, nervous system (e.g., brain, etc.), endocrine system (e.g., thyroid, etc.), soft tissues (e.g., muscle, fat, etc.), and hematopoietic system (e.g., lymphoma, myeloma, leukemia, acute lymphocytic leukemia, chronic lymphocytic leukemia, acute myeloid leukemia, chronic myeloid leukemia, etc.). For example, the peptides of the invention can be used to target agents such as therapeutic or diagnostic agents to tumors, for example, to endothelial cells that neovascularize tumors and thereby facilitate tumor growth.

As used herein, the term "diagnosis" refers to the determination of the presence of a disease or disorder in a subject. In various embodiments of the present invention, methods for making a diagnosis are provided which permit determination of the presence of a particular disease or disorder.

The term "inhibit," as used herein, means to suppress or block an activity or function by at least about ten percent relative to a control value. In various embodiments, the activity is suppressed or blocked by at least about 50%, at least about 55%, at least about 60%, at least about 65%, at least about 70%, at least about 75%, at least about 80%, at least about 85%, at least about 90%, or at least about 95%, as compared with a comparator value.

The term to "treat" as used herein, means reducing the frequency and/or severity of at least one sign or symptom experienced by a patient or subject. An appropriate therapeutic amount in any individual case may be determined by one of ordinary skill in the art using routine experimentation. As used herein, the term "treating" means ameliorating the effects of, or delaying, halting or reversing the progress of a disease or disorder. The word encompasses reducing the severity of at least one sign or symptom of a disease or disorder and/or the frequency of at least one sign or symptom of a disease or disorder.

As used herein, a "prophylactic" or "preventive" treatment is a treatment administered to a subject who does not exhibit the signs or symptoms of a disease or disorder or exhibits only early signs or symptoms of the disease or disorder for the purpose of decreasing the risk of developing additional or more severe signs of symptoms associated with the disease or disorder.

The terms "patient," "subject," "individual," and the like are used interchangeably herein, and refer to any animal, or cells thereof whether in vitro or in situ, amenable to the methods described herein. In some embodiments, the patient, subject or individual is a mammal such as a non-primate (e.g., cows, pigs, horses, cats, dogs, rats, goats, rabbits, etc.) and a primate (e.g., monkey and human), most preferably a human. In certain non-limiting embodiments, the patient, subject or individual is a human.

As used herein with respect to the compositions of the invention, "biologically active" means that the compositions elicit a biological response in a mammal that can be monitored and characterized in comparison with an untreated mammal.

As used herein, a "therapeutic" treatment is a treatment administered to a subject who exhibits signs or symptoms of a disease or disorder for the purpose of diminishing or eliminating at least one of those signs or symptoms.

An "effective amount" as used herein, means an amount which provides a therapeutic or prophylactic benefit.

The phrase "therapeutically effective amount," as used herein, refers to an amount that is sufficient or effective to prevent or treat (delay or prevent the onset of, prevent the progression of, inhibit, decrease or reverse) a disease or disorder, including alleviating signs or symptoms of such diseases or disorders. The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the terms "effective amount" or "therapeutically effective amount" or "pharmaceutically effective amount" are also used interchangeably to refer to the amount of the composition that is sufficient to provide a beneficial effect to the subject to which the composition is administered.

As used herein, the terms "therapy" or "therapeutic regimen" refer to those activities taken to alleviate or alter a disorder or disease state, e.g., a course of treatment intended to reduce or eliminate at least one sign or symptom of a disease or disorder using pharmacological, surgical, dietary and/or other techniques. A therapeutic regimen may include a prescribed dosage of one or more drugs or surgery. Therapies will most often be beneficial and reduce or eliminate at least one sign or symptom of the disorder or disease state, but in some instances the effect of a therapy will have non-desirable or side-effects. The effect of therapy will also be impacted by the physiological state of the subject, e.g., age, gender, genetics, weight, other disease conditions, etc.

As used herein, a "pharmaceutically acceptable carrier" means a pharmaceutically acceptable material, composition or carrier, such as a liquid or solid filler, diluent, excipient, solvent or encapsulating material, involved in carrying or transporting a compound(s) of the present invention within or to the subject such that it can perform its intended function. Typically, such compounds are carried or transported from one organ, or portion of the body, to another organ, or portion of the body. Each carrier must be "acceptable" in the sense of being compatible with the other ingredients of the formulation, and not injurious to the patient. Some examples of materials that can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. As used herein "pharmaceutically acceptable carrier" also includes any and all coatings, antibacterial and antifungal agents, and absorption delaying agents, and the like that are compatible with the activity of the compound, and are physiologically acceptable to the subject. Supplementary active compounds can also be incorporated into the compositions.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Remington's Pharmaceutical Sciences (1985, Genaro, ed., Mack Publishing Co., Easton, Pa.), which is incorporated herein by reference.

As used herein, the term "pharmaceutical composition" refers to a mixture of at least one compound of the invention with other chemical components and entities, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to, intravenous, oral, aerosol, parenteral, ophthalmic, pulmonary and topical administration.

"Instructional material," as that term is used herein, includes a publication, a recording, a diagram, or any other medium of expression which can be used to communicate the usefulness of the nucleic acid, polypeptide, peptide, and/or compound of the invention in the kit for identifying, diagnosing or alleviating or treating the various diseases or disorders recited herein. Optionally, or alternately, the instructional material may describe one or more methods of identifying, diagnosing or alleviating the diseases or disorders in a cell or a tissue of a subject. The instructional material of the kit may, for example, be affixed to a container that contains the nucleic acid, peptide, and/or compound of the invention or be shipped together with a container that contains the nucleic acid, peptide, and/or compound. Alternatively, the instructional material may be shipped separately from the container with the intention that the recipient uses the instructional material and the compound cooperatively.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compositions

The present invention relates in part to a tissue-targeting peptide. In one embodiment, the peptide comprises an amino acid sequence of CKPFDRALC (SEQ ID NO: 1). The present invention also relates in part to compositions comprising at least one peptide. In one embodiment, the peptide is a tissue-targeting peptide selectively targeting a biological tissue. In one embodiment, the peptide comprises an amino acid sequence of CKPFDRALC (SEQ ID NO: 1).

In one embodiment, the peptide is a peptide targeting a biological tissue. In one embodiment, the biological tissue is a connective tissue. In one embodiment, the biological tissue is a muscle tissue. In one embodiment, the biological tissue is a nervous tissue. In one embodiment, the biological tissue is an epithelial or endothelial tissue. In one embodiment, the biological tissue is a tumor tissue. In various embodiments, the biological tissue is a connective tissue, muscle tissue, nervous tissue, epithelial tissue, endothelial tissue, joint tissue, synovial tissue, inflamed joint or inflamed synovial tissue, arthritic joint or arthritic synovial tissue, neovascular tissue, neovascularized tissue (e.g., neovascularized joint or synovial tissue, neovascularized ocular—e.g., choroidal or retinal—tissue, neovascularized tumor tissue), tumor tissue, or any combination thereof.

In one embodiment, the connective tissue is a fibrous connective tissue. In one embodiment, the connective tissue is a skeletal connective tissue. In one embodiment, the connective tissue is a fluid connective tissue. In various embodiments, the connective tissue is a fibrous connective tissue, skeletal connective tissue, fluid connective tissue, or any combination thereof. In various embodiments, the biological tissue is blood, bone, tendon, ligament, adipose, areolar tissues, or any combination thereof. In various embodiments, the muscle tissue is a visceral (smooth) muscle tissue, skeletal muscle tissue, cardiac muscle tissue, or any combination thereof. In various embodiments, the nervous tissue is a brain tissue, spinal cord tissue, or any combination thereof. In various embodiments, the epithelial tissue is a simple squamous epithelium, stratified squamous epithelium, simple cuboidal epithelium, transitional epithelium, pseudostratified columnar epithelium, columnar epithelium, glandular epithelium, ciliated columnar epithelium, or any combination thereof. In various embodiments, the epithelial tissue is a skin tissue, airway tissue, reproductive tract tissue, digestive tract tissue, or any combination thereof.

In one embodiment, the peptide is a peptide targeting a biological tissue by binding to a cell of the biological tissue. In one embodiment, the peptide is a peptide targeting a cell of a biological tissue. In one embodiment, the peptide binds to a connective tissue cell. In one embodiment, the peptide binds to a muscle tissue cell. In one embodiment, the peptide binds to neuron. In one embodiment, the peptide binds to an epithelial cell. In one embodiment, the peptide binds to an endothelial cell. In one embodiment, the peptide binds to a tumor cell. In various embodiments, the peptide binds to a connective tissue cell, muscle tissue cell, neuron, epithelial cell, endothelial cell, tumor cell, or any combination thereof.

In one embodiment, the composition further comprises at least one agent. In one embodiment, the composition further comprises at least one liposome. In one embodiment, the composition further comprises at least one lipid. In one embodiment, the composition further comprises at least one pharmaceutically acceptable carrier. In various aspects of the invention, the composition further comprises at least one agent, liposome, lipid, pharmaceutically acceptable carrier, or any combination thereof.

In one embodiment, the peptide is conjugated to at least one agent. In one embodiment, the peptide is conjugated to at least one liposome. In one embodiment, the peptide is conjugated to at least one lipid. In one embodiment, the peptide is conjugated to at least one pharmaceutically acceptable carrier. In various aspects of the invention, the peptide is conjugated to at least one agent, liposome, lipid, pharmaceutically acceptable carrier, or any combination thereof.

In one embodiment, the peptide is reversibly bound to at least one agent. In one embodiment, the peptide is reversibly bound to at least one liposome. In one embodiment, the peptide is reversibly bound to at least one lipid. In one embodiment, the peptide is reversibly bound to at least one pharmaceutically acceptable carrier. In various aspects of the invention, the peptide is reversibly bound to at least one agent, liposome, lipid, pharmaceutically acceptable carrier, or any combination thereof.

In one embodiment, the agent is a protein. In one embodiment, the agent is a peptide. In one embodiment, the agent is a peptidomimetic. In one embodiment, the agent is an antibody. In one embodiment, the agent is a ribozyme. In one embodiment, the agent is a vector. In one embodiment, the agent is a nucleic acid molecule. In one embodiment, the agent is an antisense nucleic acid. In one embodiment, the agent is a small molecule drug. In one embodiment, the agent is an organic compound. In one embodiment, the agent is an inorganic compound. In various embodiments, the agent is a protein, peptide, peptidomimetic, antibody, ribozyme, vector, nucleic acid molecule, antisense nucleic acid, small molecule drug, organic compound, inorganic compound, or any combination thereof.

In one embodiment, the agent is a therapeutic agent. In one embodiment, the agent is a prophylactic agent. In one embodiment, the agent is a diagnostic agent. In one embodiment, the agent is an imaging agent. In one embodiment, the agent is a contrast agent. In one embodiment, the agent is a microparticle. In one embodiment, the agent is a nanoparticle. In various embodiments, the agent is a therapeutic agent, prophylactic agent, diagnostic agent, imaging agent, contrast agent, microparticle, nanoparticle, or any combination thereof.

In one embodiment, the therapeutic agent is glucocorticoid. In one embodiment, the therapeutic agent is a biologic. In one embodiment, the therapeutic agent is an anti-arthritis drug. In various embodiments, the therapeutic agent is glucocorticoid, biologics, anti-arthritis drug, or any combination thereof. The following are non-limiting examples of glucocorticoid that can be used to diagnose, image, or treat a disease or disorder by the disclosed methods and compositions: cortisol (hydrocortisone), cortisone, prednisone, prednisolone, methylprednisolone, dexamethasone, betamethasone, triamcinolone, fludrocortisone acetate, deoxycorticosterone acetate, or any combination thereof. The following are non-limiting examples of biologics that can be used to diagnose, image, or treat a disease or disorder by the disclosed methods and compositions: cytokines (e.g., IL-4, IL-10, IL-27, IL-35), anti-cytokine antibodies (e.g., antibodies against TNF-a, IL-1, IL-6, IL-17A, IL-17F, IL-22), and anti-cytokine receptor antibodies (e.g., antibodies against IL-6 receptor).

In various embodiments, the contrast agent is a radiocontrast medium, iodinated contrast agent, iodine, ipodate sodium, diatrizoate, metrizoate, iothalamate, ioxaglate, iopamidol, iohexol, ioxilan, iopromide, iodixanol, ioversol, barium, MRI contrast agent, gadolinium, ultrasound contrast agent, saline solution, or any combination thereof.

In one embodiment, the agent is an imaging agent. The following are non-limiting examples of imaging agents that can be used to image a disease or disorder by the disclosed methods and compositions: Ca-47-$Ca^{2+}$, C11-L-methyl-methionine, C14-glycocholic acid, C14-PABA (para-amino benzoic acid), C14-urea, C14-d-xylose, Cr51, Cr51-$Cr^{3+}$, Cr51-EDTA (ethylenediaminetetraacetic acid), Co57-cyanocobalamin (vitamin B12), Co58-cyanocobalamin (vitamin B12), Er169-colloid, F18-FDG (fluorodeoxyglucose), F18-sodium fluoride, F18-fluorocholine, F18-desmethoxyfallypride, Ga67-$Ga^{3+}$, Ga68-dotatoc, Ga68-dotatate, Ga68-PSMA, H3-water, In111-DTPA (diethylenetriaminepentaacetic acid), In111-leukocytes, In111-platelets, In111-pentetreotide, In111-octreotide, I123-iodide, I123-o-iodohippurate, I123-MIBG (m-iodobenzylguanidine), I123-FP-CIT, I125-fibrinogen, I131-iodide, I131-MIBG (m-iodobenzylguanidine), Fe59-$Fe^{2+}$, Fe59-$Fe^{3+}$, Kr81m-gas, Kr-81m-aqueous solution, $^{177}$Lu-DOTA-TATE, N13-ammonia, O15-water, P32-phosphate, Ra223 cation, $^{223}RaCl_2$, Rb-82 chloride, Sm153-EDTMP (ethylenediaminotetramethylenephosphoric acid), Se75-selenorcholesterol, Se75-SeHCAT (23-seleno-25-homo-tauro-cholate), Na22-Na$^+$, Na24-Na$^+$, Sr89-chloride, Tc99m-pertechnetate, Tc99m-human albumin, Tc99m-Human albumin macroaggregates, Tc99m-Human albumin microspheres, Tc99m-phosphonates, Tc99m-phosphates (MDP/HDP), Tc99m-DTPA (diethylenetriaminepenta-acetic acid), Tc99m-DMSA (V) (dimercaptosuccinic acid), Tc99m-DMSA(III) (dimercaptosuccinic acid), Tc99m-colloid, Tc99m-HIDA (hepatic iminodiacetic acid), Tc99m-denatured (heat damaged) red blood cells, Tc99m-whole red blood cells, Tc99m-MAG3 (mercaptoacetyltriglycine), Tc99m-exametazime (HMPAO), Tc99m-Exametazime labelled leucocytes, Tc99m-sestamibi (MIBI-methoxy isobutyl isonitrile), Tc99m-Sulesomab (IMMU-MN3 murine Fab'-SH antigranulocyte monoclonal antibody fragments), Tc99m-technegas, Tc99m-human immunoglobulin, Tc99m-tetrofosmin, Tc99m-ECD (ethyl cysteinate dimer), T1201-Tl$^+$, Xe133-gas, Xe133 in isotonic sodium chloride solution, Y90-silicate, and any combination thereof.

Imaging agents are materials that allow for visualization after exposure to a cell or tissue. Visualization includes imaging for the naked eye, as well as imaging that requires detecting with instruments or detecting information not normally visible to the eye, and includes imaging that requires detecting of photons, sound or other energy quanta. Examples include stains, vital dyes, fluorescent markers, radioactive markers, enzymes or plasmid constructs encoding markers or enzymes. Many materials and methods for imaging and targeting that may be used in the composition of the invention are provided in the Handbook of Targeted delivery of Imaging Agents, Torchilin, ed. (1995) CRC Press, Boca Raton, Fla. Visualization based on molecular imaging typically involves detecting biological processes or biological molecules at a tissue, cell, or molecular level. Molecular imaging can be used to assess specific targets for gene therapies, cell-based therapies, and to visualize pathological conditions as a diagnostic or research tool. Imaging agents that are able to be delivered intracellularly are particularly useful because such agents can be used to assess intracellular activities or conditions. Suitable imaging agents include, for example, fluorescent molecules, labeled antibodies, labeled avidin:biotin binding agents, colloidal metals (e.g., gold, silver), reporter enzymes (e.g., horseradish peroxidase), superparamagnetic transferrin, second reporter systems (e.g., tyrosinase), and paramagnetic chelates. In some embodiments, the imaging agent is a Magnetic resonance imaging contrast agent. Examples of Magnetic resonance imaging contrast agents include, but are not limited to, 1,4,7,10-tetraazacyclododecane-N,N',N'',N'''-tetraacetic acid (DOTA), diethylenetriaminepentaacetic (DTPA), 1,4,7,10-tetraazacyclododecane-N,N',N'',N'''-tetraethylphosphorus (DOTEP), 1,4,7,10-tetraazacyclododecane-N,N',N''-triaacetic acid (DOTA) and derivatives thereof (see U.S. Pat. Nos. 5,188,816, 5,219,553, and 5,358,704). In some embodiments, the imaging agent is an X-Ray contrast agent. X-ray contrast agents already known in the art include a number of halogenated derivatives, especially iodinated derivatives, of 5-amino-isophthalic acid.

Exemplary detectable labels include, but are not limited to biotin, an enzyme, an epitope, a radionuclide, a fluorescent molecule, and the like.

In certain embodiments, the composition comprises an imaging agent that may be further attached to a detectable label (e.g., the label can be a radioisotope, fluorescent compound, enzyme or enzyme co-factor). The active moiety may be a radioactive agent, such as: radioactive heavy metals such as iron chelates, radioactive chelates of gadolinium or manganese, positron emitters of oxygen, nitrogen, iron, carbon, or gallium, $^{43}$K, $^{52}$Fe, $^{57}$Co, $^{67}$Cu, $^{67}$Ga, $^{68}$Ga, $^{123}$I, $^{125}$I, $^{131}$I, $^{132}$I, or $^{99}$Tc. A composition including such a moiety may be used as an imaging agent and be administered in an amount effective for diagnostic use in a mammal such as a human. In this manner, the localization and accumulation of the imaging agent can be detected. The localization and accumulation of the imaging agent may be detected by radioscintography, nuclear magnetic resonance imaging, computed tomography, or positron emission tomography. As will be evident to the skilled artisan, the amount of radioisotope to be administered is dependent upon the radioisotope. Those having ordinary skill in the art can readily formulate the amount of the imaging agent to be administered based upon the specific activity and energy of a given radionuclide used as the active moiety. Typically, 0.1-100 millicuries per dose of imaging agent, preferably 1-10 millicuries, most often 2-5 millicuries are administered. Thus, compositions according to the present invention useful as imaging agents comprising a targeting moiety conjugated to a radioactive moiety comprise 0.1-100 millicuries, in some embodiments preferably 1-10 millicuries, in some embodiments preferably 2-5 millicuries, in some embodiments more preferably 1-5 millicuries.

The means of detection used to detect the label is dependent of the nature of the label used and the nature of the biological sample used, and may also include fluorescence polarization, high performance liquid chromatography, antibody capture, gel electrophoresis, differential precipitation, organic extraction, size exclusion chromatography, fluorescence microscopy, or fluorescence activated cell sorting (FACS) assay.

The targeting peptides of the present invention further include conservative variants of the targeting peptides herein described. As used herein, a "conservative variant" refers to alterations in the amino acid sequence that do not substantially and adversely affect the binding or association capacity of the peptide. A substitution, insertion or deletion is said to adversely affect the peptide when the altered sequence prevents, reduces, or disrupts a function or activity associated with the peptide. For example, the overall charge, structure or hydrophobic-hydrophilic properties of the peptide can be altered without adversely affecting an activity. Accordingly, the amino acid sequence can be altered, for example to render the peptide more hydrophobic or hydrophilic, without adversely affecting the activities of the peptide.

These variants, though possessing a slightly different amino acid sequence than those recited elsewhere herein, will still have the same or similar properties associated with any of the peptides discussed herein. Ordinarily, the conservative substitution variants, will have an amino acid sequence having at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity with any of the peptides discussed elsewhere herein.

In certain embodiments, the composition comprises a fragment of one or more of the peptides discussed elsewhere herein. For example, in certain embodiments, the fragment comprises 2 or more, 3 or more, 4 or more, 5 or more, 6 or more, 7 or more, 8 or more, 9 or more, 10 or more, 15 or more, or 20 or more amino acid residues of one of any of the peptides discussed elsewhere herein.

The peptide may comprise one or more hydrophilic residues. For example, in certain embodiments, the peptide comprises 1 or more, 2 or more, 3 or more, 4 or more, 5 or more, 6 or more, 7 or more, 8 or more, 9 or more, 10 or more, 15 or more, or 20 or more hydrophilic amino acid residues. The hydrophilic amino acid residues may be consecutive or non-consecutive. In certain embodiments, the peptide is enriched in hydrophilic residues. For example, in certain embodiments, the peptide comprises 40% or more, 50% or more, 60% or more, 70% or more, 75% or more, 80% or more, 85% or more, 90% or more, or 95% or more hydrophilic residues.

In some embodiments, the composition, for example the tissue-targeting peptide of the composition, are able to associate with (or bind to) specific sequences of DNA or other proteins. These peptides may be able to bind, for example, to DNA or other proteins with high affinity and selectivity. As used herein, the term "bind" or "binding" refers to the specific association or other specific interaction between two molecular species, such as, but not limited to, protein-DNA interactions and protein-protein interactions, for example, the specific association between proteins and their DNA targets, receptors and their ligands, enzymes and their substrates, etc. Such binding may be specific or non-specific, and can involve various noncovalent interactions, such as including hydrogen bonding, metal coordination, hydrophobic forces, van der Waals forces, pi-pi interactions, and/or electrostatic effects. It is contemplated that such association may be mediated through specific sites on each of two (or more) interacting molecular species. Binding can be mediated by structural and/or energetic components. In some cases, the latter will comprise the interaction of molecules with opposite charges.

The peptide of the present invention may be made using chemical methods. For example, peptides can be synthesized by solid phase techniques (Roberge J Y et al (1995) Science 269: 202-204), cleaved from the resin, and purified by preparative high performance liquid chromatography. Automated synthesis may be achieved, for example, using the ABI 431 A Peptide Synthesizer (Perkin Elmer) in accordance with the instructions provided by the manufacturer.

The peptide may alternatively be made by recombinant means or by cleavage from a longer polypeptide. The composition of a peptide may be confirmed by amino acid analysis or sequencing.

The variants of the polypeptides according to the present invention may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the polypeptide is an alternative splice variant of the polypeptide of the present invention, (iv) fragments of the polypeptides and/or (v) one in which the polypeptide is fused with another polypeptide, such as a leader or secretory sequence or a sequence which is employed for purification (for example, His-tag) or for detection (for example, Sv5 epitope tag). The fragments include polypeptides generated via proteolytic cleavage (including multi-site proteolysis) of an original sequence. Variants may be post-translationally, or chemically modified. Such variants are deemed to be within the scope of those skilled in the art from the teaching herein.

The use of lipid formulations is contemplated for the introduction of nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Chol") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Liposomes, in one embodiment, increase intracellular stability, increase uptake efficiency and improve biological activity. In another embodiment, liposomes are hollow spherical vesicles composed of lipids arranged in a similar fashion as those lipids which make up the cell membrane. They have, in another embodiment, an internal aqueous space for entrapping water-soluble compounds and range in size from 0.05 to several microns in diameter. In another embodiment, liposomes can deliver peptides to cells in a biologically active form.

Peptide Analogs

The present invention relates to peptide analogs of a peptide comprising the amino acid sequence of SEQ ID NO: 1, or any another peptide appropriate for use with the invention and uses thereof. For example, in certain instances the invention provides peptides and peptide analogs based on fragments, analogs, or derivatives of a peptide comprising SEQ ID NO: 1, where the peptides and peptide analogs exhibit desirable properties. In one embodiment, the invention provides compositions comprising peptides and analogs, fragments, and derivatives thereof that exhibit one or more of improved solubility, half-life, bioavailability, reduced renal clearance and the like compared with the peptide comprising the amino acid sequence of SEQ ID NO: 1. In one embodiment, the invention provides compositions comprising peptides and analogs, fragments, and derivatives thereof that exhibit one or more of improved solubility, half-life, bioavailability, reduced renal clearance and the like compared with the peptide comprising the amino acid sequence of SEQ ID NO: 1.

A peptide or chimeric protein of the invention may be phosphorylated using conventional methods such as the method described in Reedijk et al. (The EMBO Journal 11(4):1365, 1992).

Cyclic derivatives of the peptides or chimeric proteins of the invention are also part of the present invention. Cyclization may allow the peptide or chimeric protein to assume a more favorable conformation for association with other molecules. Cyclization may be achieved using techniques known in the art. For example, disulfide bonds may be formed between two appropriately spaced components having free sulfhydryl groups, or an amide bond may be formed between an amino group of one component and a carboxyl group of another component. Cyclization may also be achieved using an azobenzene-containing amino acid as described by Ulysse, L., et al., J. Am. Chem. Soc. 1995, 117, 8466-8467. The components that form the bonds may be side chains of amino acids, non-amino acid components or a combination of the two. In an embodiment of the invention, cyclic peptides may comprise a beta-turn in the right position. Beta-turns may be introduced into the peptides of the invention by adding the amino acids Pro-Gly at the right position.

It may be desirable to produce a cyclic peptide which is more flexible than the cyclic peptides containing peptide bond linkages as described above. A more flexible peptide may be prepared by introducing cysteines at the right and left position of the peptide and forming a disulfide bridge between the two cysteines. The two cysteines are arranged so as not to deform the beta-sheet and turn. The peptide is more flexible as a result of the length of the disulfide linkage and the smaller number of hydrogen bonds in the beta-sheet portion. The relative flexibility of a cyclic peptide can be determined by molecular dynamics simulations.

In one embodiment, the subject compositions are peptidomimetics of the peptides of the invention, for example, peptidomimetics of the peptide comprising the amino acid sequence of SEQ ID NO: 1. Peptidomimetics are compounds based on, or derived from, peptides and proteins. The peptidomimetics of the present invention typically can be obtained by structural modification of a known peptide sequence using unnatural amino acids, conformational restraints, isosteric replacement, and the like. The subject peptidomimetics constitute the continuum of structural space between peptides and non-peptide synthetic structures; peptidomimetics may be useful, therefore, in delineating pharmacophores and in helping to translate peptides into nonpeptide compounds with the activity of the parent peptides.

The peptidomimetics of the invention may include unnatural amino acids formed by post-translational modification or by introducing unnatural amino acids during translation. A variety of approaches are available for introducing unnatural amino acids during protein translation. By way of example, special tRNAs, such as tRNAs which have suppressor properties, suppressor tRNAs, have been used in the process of site-directed non-native amino acid replacement (SNAAR). In SNAAR, a unique codon is required on the mRNA and the suppressor tRNA, acting to target a non-native amino acid to a unique site during the protein synthesis (described in WO90/05785). However, the suppressor tRNA must not be recognizable by the aminoacyl tRNA synthetases present in the protein translation system. In certain cases, a non-native amino acid can be formed after the tRNA molecule is aminoacylated using chemical reactions which specifically modify the native amino acid and do not significantly alter the functional activity of the aminoacylated tRNA. These reactions are referred to as post-aminoacylation modifications. For example, the epsilon-amino group of the lysine linked to its cognate tRNA (tRNALYS), could be modified with an amine specific photoaffinity label.

Nucleic Acid Therapeutic Agents

The present invention also relates in part to a composition comprising an isolated nucleic acid molecule encoding a tissue-targeting peptide. In one aspect of the invention, the isolated nucleic acid molecule encodes a tissue-targeting peptide, the peptide comprising the amino acid sequence of (SEQ ID NO: 1). The present invention further provides, in another embodiment, nucleic acid molecules that encode any of the amino acid sequences discussed herein. As used herein, "nucleic acid" includes cDNA and mRNA, as well as nucleic acids based on alternative backbones or including alternative bases whether derived from natural sources or synthesized. Those of ordinary skill in the art, given an amino acid sequence, will be able to generate corresponding nucleic acid sequences that can be used to generate the amino acid sequence, using no more than routine skill.

In one embodiment, the composition comprises a nucleic acid molecule encoding a peptide comprising the amino acid sequence of SEQ ID NO: 1. In one embodiment, the nucleic acid molecule encodes a peptide comprising an amino acid sequence having substantial homology to SEQ ID NO: 1. For example, in one embodiment, the nucleic acid molecule encodes a peptide comprising an amino acid sequence having at least about 75%, at least about 80%, at least about 85%, at least about 90%, at least about 95%, at least about 98%, or at least about 99% sequence identity with any of the peptides describe elsewhere herein.

For example, in one embodiment the nucleic acid molecule encodes a peptide comprising an amino acid molecule comprising 2 or more, 3 or more, 4 or more, 5 or more, 6 or more, 7 or more, 8 or more, 9 or more, 10 or more, 15 or more, or 20 or more amino acid residues of one of any of the peptides discussed elsewhere herein.

Modifications to the primary structure itself by deletion, addition, or alteration of the amino acids incorporated into the peptide sequence during translation can be made without destroying the activity of the peptide. Such substitutions or other alterations result in peptides having an amino acid sequence encoded by a nucleic acid falling within the contemplated scope of the present invention.

The present invention further provides, in some embodiments, recombinant DNA molecules that contain a coding sequence. As used herein, a "recombinant DNA molecule" is a DNA molecule that has been subjected to molecular manipulation. Methods for generating recombinant DNA molecules are well known in the art, for example, see Sambrook et al., 2012, Molecular Cloning: A Laboratory Manual, Cold Spring Harbor Laboratory, New York. In some recombinant DNA molecules, a coding DNA sequence is operably linked to expression control sequences and vector sequences.

The choice of vector and expression control sequences to which one of the peptide family encoding sequences of the present invention is operably linked depends directly, as is well known in the art, on the functional properties desired (e.g., protein expression, and the host cell to be transformed). A vector of the present invention may be at least capable of directing the replication or insertion into the host chromosome, and preferably also expression, of the structural gene included in the recombinant DNA molecule.

Expression control elements that are used for regulating the expression of an operably linked protein encoding sequence are known in the art and include, but are not limited to, inducible promoters, constitutive promoters, secretion signals, and other regulatory elements. In some embodiments, the inducible promoter is readily controlled, such as being responsive to a nutrient in the host cell's medium.

In one embodiment, the vector containing a coding nucleic acid molecule will include a prokaryotic replicon, i.e., a DNA sequence having the ability to direct autonomous replication and maintenance of the recombinant DNA molecule extra-chromosomal in a prokaryotic host cell, such as a bacterial host cell, transformed therewith. Such replicons are well known in the art. In addition, vectors that include a prokaryotic replicon may also include a gene whose expression confers a detectable marker such as a drug resistance. Typical of bacterial drug resistance genes are those that confer resistance to ampicillin or tetracycline.

Vectors that include a prokaryotic replicon can further include a prokaryotic or bacteriophage promoter capable of directing the expression (transcription and translation) of the coding gene sequences in a bacterial host cell, such as *E. coli*. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Any suitable prokaryotic host can be used to express a recombinant DNA molecule encoding a peptide of the invention.

Expression vectors compatible with eukaryotic cells, including those compatible with vertebrate cells, can also be used to form recombinant DNA molecules that contain a coding sequence. Eukaryotic cell expression vectors are well known in the art and are available from several commercial sources. Typically, such vectors are provided containing convenient restriction sites for insertion of the desired DNA segment.

Eukaryotic cell expression vectors used to construct the recombinant DNA molecules of the present invention may further include a selectable marker that is effective in a eukaryotic cell, such as a drug resistance selection marker. An example drug resistance marker is the gene whose expression results in neomycin resistance, i.e., the neomycin phosphotransferase (neo) gene. Alternatively, the selectable marker can be present on a separate plasmid, the two vectors introduced by co-transfection of the host cell, and transfectants selected by culturing in the appropriate drug for the selectable marker.

The present invention further provides, in still another embodiment, methods for producing a peptide of the invention using nucleic acid molecules herein described. In general terms, the production of a recombinant form of a peptide typically involves the following steps: a nucleic acid molecule is obtained that encodes a peptide of the invention.

The nucleic acid molecule may then be placed in operable linkage with suitable control sequences, as described above, to form an expression unit containing the peptide open reading frame. The expression unit is used to transform a suitable host and the transformed host is cultured under conditions that allow the production of the recombinant peptide. Optionally the recombinant peptide is isolated from the medium or from the cells; recovery and purification of the peptide may not be necessary in some instances where some impurities may be tolerated.

Each of the foregoing steps can be done in a variety of ways. The construction of expression vectors that are operable in a variety of hosts is accomplished using appropriate replicons and control sequences, as set forth above. The control sequences, expression vectors, and transformation methods are dependent on the type of host cell used to express the gene. Suitable restriction sites, if not normally available, can be added to the ends of the coding sequence, so as to provide an excisable gene to insert into these vectors. An artisan of ordinary skill in the art can readily adapt any host/expression system known in the art for use with the nucleic acid molecules of the invention to produce a recombinant peptide.

Fusion Constructs

The present invention also provides a composition for targeted delivery of an agent. In one embodiment, the composition comprises at least one peptide conjugated to a therapeutically effective amount of at least one agent. In one embodiment, the composition comprises at least one peptide conjugated to a therapeutically effective amount of at least one liposome. In one embodiment, the composition comprises at least one peptide conjugated to a therapeutically effective amount of at least one lipid. In one embodiment, the composition comprises at least one peptide conjugated to a therapeutically effective amount of at least one pharmaceutically acceptable carrier. In various embodiments, the composition comprises at least one peptide conjugated to a therapeutically effective amount of at least one agent, liposome, lipid, pharmaceutically acceptable carrier, or any combination thereof. In one embodiment, the peptide is a tissue-targeting peptide comprising an amino acid sequence of CKPFDRALC (SEQ ID NO: 1).

A peptide of the invention may be fused with, linked to, or conjugated with other molecules, to prepare fusion constructs. This may be accomplished, for example, by the synthesis of N-terminal or C-terminal fusion constructs provided that the resulting fusion construct retains the tissue-targeting function of the peptide.

In one embodiment, the composition comprises a construct comprising one or more agents fused with, linked to, or conjugated with, one or more tissue-targeting peptides described elsewhere herein. The one or more agents may include, but is not limited to, therapeutic agents, prophylactic agents, chemotherapeutic agents, diagnostic agents, imaging agents, radiosensitizing agents, contrast agents, drug delivery vehicles, liposomes, polymerosomes, micelles, microparticles, nanoparticles, and the like. Exemplary agents include, but is not limited to, peptides, nucleic acid molecule, antisense nucleic acid molecules, small molecule drugs, organic compounds, inorganic compounds, antibodies, vitamins, hormones, cytokines, growth factors, detectable labels, quantum dots, and the like.

The tissue-targeting peptide may be linked to the agent using any methodology known in the art, including, but not limited to, covalent linkage, non-covalent linkage, cross-linking, peptide linkers, nucleotide linkers, and the like. Linkages can include but are not limited to isothiocyanate, NHS, haloacetyl, maleimide or other thiolation linkers, disulfide, glucuronide linkage, acid sensitive linkers (e.g., hydrazone), enzyme cleavable linkers (Val-Cit dipeptide, linkages cleavable by matrix metalloproteinases and cathepsin proteases), and click chemistry linkages.

Exemplary therapeutic agents include, but are not limited to analgesics, anesthetics, antifungals, antibiotics, anti-inflammatories, anthelmintics, antidotes, antiemetics, antihistamines, antihypertensives, antimalarials, antimicrobials, antipsychotics, antipyretics, antiseptics, antiarthritics, antituberculotics, antitussives, antivirals, bronchodialators, cardioactive drugs, cathartics, chemotherapeutic agents, a colored or fluorescent imaging agent, corticoids (such as steroids), antidepressants, depressants, diagnostic aids, diuretics, enzymes, expectorants, hormones, hypnotics, minerals, nutritional supplements, parasympathomimetics, potassium supplements, radiation sensitizers, a radioisotope, sedatives, sulfonamides, stimulants, sympathomimetics, tranquilizers, urinary anti-infectives, vasoconstrictors, vasodilators, vitamins, xanthine derivatives, and the like.

Small Molecule Therapeutic Agents

In various embodiments, the therapeutic agent is a small molecule. When the therapeutic agent is a small molecule, a small molecule may be obtained using standard methods known to the skilled artisan. Such methods include chemical organic synthesis or biological means. Biological means include purification from a biological source, recombinant synthesis and in vitro translation systems, using methods well known in the art. In one embodiment, a small molecule therapeutic agents comprises an organic molecule, inorganic molecule, biomolecule, synthetic molecule, and the like.

Combinatorial libraries of molecularly diverse chemical compounds potentially useful in treating a variety of diseases and conditions are well known in the art as are method of making the libraries. The method may use a variety of techniques well-known to the skilled artisan including solid phase synthesis, solution methods, parallel synthesis of single compounds, synthesis of chemical mixtures, rigid core structures, flexible linear sequences, deconvolution strategies, tagging techniques, and generating unbiased molecular landscapes for lead discovery vs. biased structures for lead development.

In a general method for small library synthesis, an activated core molecule is condensed with a number of building blocks, resulting in a combinatorial library of covalently linked, core-building block ensembles. The shape and rigidity of the core determines the orientation of the building blocks in shape space. The libraries can be biased by changing the core, linkage, or building blocks to target a characterized biological structure ("focused libraries") or synthesized with less structural bias using flexible cores.

The small molecules and small molecule compounds described herein may be present as salts even if salts are not depicted and it is understood that the invention embraces all salts and solvates of the inhibitors depicted here, as well as the non-salt and non-solvate form of the inhibitors, as is well understood by the skilled artisan. In some embodiments, the salts of the inhibitors of the invention are pharmaceutically acceptable salts.

Where tautomeric forms may be present for any of the inhibitors described herein, each and every tautomeric form is intended to be included in the present invention, even though only one or some of the tautomeric forms may be explicitly depicted. For example, when a 2-hydroxypyridyl moiety is depicted, the corresponding 2-pyridone tautomer is also intended.

The invention also includes any or all of the stereochemical forms, including any enantiomeric or diasteriomeric forms of the inhibitors described. The recitation of the structure or name herein is intended to embrace all possible stereoisomers of inhibitors depicted. All forms of the inhibitors are also embraced by the invention, such as crystalline or non-crystalline forms of the inhibitors. Compositions comprising an inhibitor of the invention are also intended, such as a composition of substantially pure inhibitor, including a specific stereochemical form thereof, or a composition comprising mixtures of inhibitors of the invention in any ratio, including two or more stereochemical forms, such as in a racemic or non-racemic mixture.

In one embodiment, the small molecule therapeutic agent of the composition comprises an analog or derivative of a therapeutic agent described herein. In one embodiment, the small molecules described herein are candidates for derivatization. As such, in certain instances, the analogs of the small molecules described herein that have modulated potency, selectivity, and solubility are included herein and provide useful leads for drug discovery and drug development. Thus, in certain instances, during optimization new analogs are designed considering issues of drug delivery, metabolism, novelty, and safety.

In some instances, small molecule therapeutic agents described herein are derivatized/analoged as is well known in the art of combinatorial and medicinal chemistry. The analogs or derivatives can be prepared by adding and/or substituting functional groups at various locations. As such, the small molecules described herein can be converted into derivatives/analogs using well known chemical synthesis procedures. For example, all of the hydrogen atoms or substituents can be selectively modified to generate new analogs. Also, the linking atoms or groups can be modified into longer or shorter linkers with carbon backbones or hetero atoms. Also, the ring groups can be changed so as to have a different number of atoms in the ring and/or to include hetero atoms. Moreover, aromatics can be converted to cyclic rings, and vice versa. For example, the rings may be from 5-7 atoms, and may be homocycles or heterocycles.

In one embodiment, the small molecule therapeutic agents described herein can independently be derivatized/analoged by modifying hydrogen groups independently from each other into other substituents. That is, each atom on each molecule can be independently modified with respect to the other atoms on the same molecule. Any traditional modification for producing a derivative/analog can be used. For example, the atoms and substituents can be independently comprised of hydrogen, an alkyl, aliphatic, straight chain aliphatic, aliphatic having a chain hetero atom, branched aliphatic, substituted aliphatic, cyclic aliphatic, heterocyclic aliphatic having one or more hetero atoms, aromatic, heteroaromatic, polyaromatic, polyamino acids, peptides, polypeptides, combinations thereof, halogens, halo-substituted aliphatics, and the like. Additionally, any ring group on a compound can be derivatized to increase and/or decrease ring size as well as change the backbone atoms to carbon atoms or hetero atoms.

In other related aspects, the therapeutic agent is an isolated nucleic acid. In certain embodiments, the isolated nucleic acid molecule is one of a DNA molecule or an RNA molecule. In certain embodiments, the isolated nucleic acid molecule is a cDNA, mRNA, or miRNA molecule. In one embodiment, the therapeutic agent is an isolated nucleic acid encoding a therapeutic peptide. For example, in certain embodiments, the present invention provides a gene therapy composition comprising the tissue-targeting peptide described herein.

In some instances, the therapeutic agent is an siRNA, miRNA, or antisense molecule, which inhibits a targeted nucleic acid. In one embodiment, the nucleic acid comprises a promoter/regulatory sequence such that the nucleic acid is preferably capable of directing expression of the nucleic acid. Thus, the invention encompasses expression vectors and methods for the introduction of exogenous DNA into cells with concomitant expression of the exogenous DNA in the cells such as those described, for example, in Sambrook et al. (2012, Molecular Cloning: A Laboratory Manual, Cold Spring Harbor Laboratory, New York), and in Ausubel et al. (1997, Current Protocols in Molecular Biology, John Wiley & Sons, New York) and as described elsewhere herein.

In one embodiment, the therapeutic agent is an siRNA. RNA interference (RNAi) is a phenomenon in which the introduction of double-stranded RNA (dsRNA) into a diverse range of organisms and cell types causes degradation of the complementary mRNA. In the cell, long dsRNAs are cleaved into short 21-25 nucleotide small interfering RNAs, or siRNAs, by a ribonuclease known as Dicer. The siRNAs subsequently assemble with protein components into an RNA-induced silencing complex (RISC), unwinding in the process. Activated RISC then binds to complementary transcript by base pairing interactions between the siRNA antisense strand and the mRNA. The bound mRNA is cleaved and sequence specific degradation of mRNA results in gene silencing. See, for example, U.S. Pat. No. 6,506,559; Fire et al., 1998, Nature 391(19):306-311; Timmons et al., 1998, Nature 395:854; Montgomery et al., 1998, TIG 14 (7):255-258; David R. Engelke, Ed., RNA Interference (RNAi) Nuts & Bolts of RNAi Technology, DNA Press, Eagleville, P A (2003); and Gregory J. Hannon, Ed., RNAi A Guide to Gene Silencing, Cold Spring Harbor Laboratory Press, Cold Spring Harbor, N.Y. (2003). Soutschek et al. (2004, Nature 432:173-178) describe a chemical modification to siRNAs that aids in intravenous systemic delivery. Optimizing siRNAs involves consideration of overall G/C content, C/T content at the termini, Tm and the nucleotide content of the 3' overhang. See, for instance, Schwartz et al., 2003, Cell, 115:199-208 and Khvorova et al., 2003, Cell 115:209-216. Therefore, the present invention also includes methods of decreasing levels of PTPN22 using RNAi technology.

In one embodiment, the therapeutic agent is a short hairpin RNA (shRNA) therapeutic agent. shRNA molecules are well known in the art and are directed against the mRNA of a target, thereby decreasing the expression of the target. In certain embodiments, the encoded shRNA is expressed by a cell, and is then processed into siRNA. For example, in certain instances, the cell possesses native enzymes (e.g., dicer) that cleaves the shRNA to form siRNA.

In one embodiment of the invention, an antisense nucleic is used as a therapeutic agent to inhibit the expression of a target protein. The antisense expressing vector is used to transfect a mammalian cell or the mammal itself, thereby causing reduced endogenous expression of the target protein.

Antisense molecules and their use for inhibiting gene expression are well known in the art (see, e.g., Cohen, 1989, In: Oligodeoxyribonucleotides, Antisense Inhibitors of Gene Expression, CRC Press). Antisense nucleic acids are DNA or RNA molecules that are complementary, as that term is defined elsewhere herein, to at least a portion of a specific mRNA molecule (Weintraub, 1990, Scientific American 262:40). In the cell, antisense nucleic acids hybridize to the corresponding mRNA, forming a double-stranded molecule thereby inhibiting the translation of genes.

The use of antisense methods to inhibit the translation of genes is known in the art, and is described, for example, in Marcus-Sakura (1988, Anal. Biochem. 172:289). Such antisense molecules may be provided to the cell via genetic expression using DNA encoding the antisense molecule as taught by Inoue, 1993, U.S. Pat. No. 5,190,931.

Alternatively, antisense molecules of the invention may be made synthetically and then provided to the cell. Antisense oligomers of between about 10 to about 30, and more preferably about 15 nucleotides, are preferred, since they are easily synthesized and introduced into a target cell. Synthetic antisense molecules contemplated by the invention include oligonucleotide derivatives known in the art which have improved biological activity compared to unmodified oligonucleotides (see U.S. Pat. No. 5,023,243).

In one embodiment of the invention, a ribozyme is used as a therapeutic agent to inhibit expression of a target protein. Ribozymes useful for inhibiting the expression of a target molecule may be designed by incorporating target sequences into the basic ribozyme structure, which are complementary, for example, to the mRNA sequence encoding the target molecule. Ribozymes targeting the target molecule, may be synthesized using commercially available reagents (Applied Biosystems, Inc., Foster City, Calif.) or they may be genetically expressed from DNA encoding them.

In one embodiment, the therapeutic agent may comprise one or more components of a CRISPR-Cas system, where a guide RNA (gRNA) targeted to a gene encoding a target molecule, and a CRISPR-associated (Cas) peptide form a complex to induce mutations within the targeted gene. In one embodiment, the therapeutic agent comprises a gRNA or a nucleic acid molecule encoding a gRNA. In one embodiment, the therapeutic agents comprises a Cas peptide or a nucleic acid molecule encoding a Cas peptide.

In other related aspects, the therapeutic agent includes an isolated peptide that modulates a target. For example, in one embodiment, the peptide of the invention inhibits or activates a target directly by binding to the target thereby modulating the normal functional activity of the target. In another embodiment, the peptide of the invention modulates the target by competing with endogenous proteins. In yet another embodiment, the peptide of the invention modulates the activity of the target by acting as a transdominant negative mutant.

In one embodiment, the therapeutic agent is an antibody. In certain embodiments, the antibody can inhibit a target to provide a beneficial effect. The antibodies may be intact monoclonal or polyclonal antibodies, and immunologically active fragments (e.g., a Fab or (Fab)2 fragment), an antibody heavy chain, an antibody light chain, humanized antibodies, a genetically engineered single chain FV molecule (Ladner et al, U.S. Pat. No. 4,946,778), or a chimeric antibody, for example, an antibody which contains the binding specificity of a murine antibody, but in which the remaining portions are of human origin. Antibodies including monoclonal and polyclonal antibodies, fragments and chimeras, may be prepared using methods known to those skilled in the art. Antibodies can be prepared using intact polypeptides or fragments containing an immunizing antigen of interest. The polypeptide or oligopeptide used to immunize an animal may be obtained from the translation of RNA or synthesized chemically and can be conjugated to a carrier protein, if desired. Suitable carriers that may be chemically coupled to peptides include bovine serum albumin and thyroglobulin, keyhole limpet hemocyanin. The coupled polypeptide may then be used to immunize the animal (e.g., a mouse, a rat, or a rabbit).

In certain embodiments, the peptide is fused to, linked to, a drug delivery vehicle, wherein the vehicle comprises an agent, for example, a therapeutic agent, prophylactic agent, imaging agent, or contrast agent.

In certain embodiments, the one or more agents may be linked to the tissue-targeting peptide using any known methodology known in the art. The one or more agents may be directly or indirectly linked or conjugated to the tissue-targeting peptide. For example, in certain embodiments, the one or more agents may be linked to the tissue-targeting peptide via a linker peptide sequence.

In one embodiment, the composition comprises the tissue-targeting peptide described herein and one or more targeting moieties. For example, the one or more targeting moieties can be any moiety recognized by a transmembrane or intracellular receptor protein. In one embodiment, a targeting moiety is a ligand. The ligand, according to the present invention, preferentially binds to and/or internalizes into a cell in which the attached nucleic acid by way of the interaction with the densely packed cationic amino acid residues enters the cell. A ligand is usually a member of a binding pair where the second member is present on, or in a target cell, or in a tissue comprising the target cell. Examples of ligands suitable for the present invention are: folic acid, protein (e.g., transferrin), growth factor, enzyme, peptide, receptor, antibody or antibody fragment, such as Fab', Fv, single chain Fv, single-domain antibody, or any other polypeptide comprising antigen-binding sequences (CDRs) of an antibody molecule. In one embodiment, the targeting moiety specifically interacts with a growth factor receptor, an angiogenic factor receptor, a transferrin receptor, a cell adhesion molecule, or a vitamin receptor. The choice of targeting moiety depends upon the type and number of ligands that define the surface of a target cell. For example, the targeting moiety may be chosen to recognize a ligand that acts as a cell surface marker on target cells associated with a particular disease state. Thus, examples of cell surface markers that may act as ligands for the targeting moiety in the composition of the invention include those associated with viral, bacterial and parasitic infections, autoimmune disease and cancer cells.

The one or more agents may comprise an antibiotic, such as tobramycin, colistin, or aztreonam. The one or more agents may comprise one or more inhaled corticosteroids, such as flunisolide, triamcinolone acetonide, beclomethasone dipropionate, mometasone, budesonide, ciclesonide, or fluticasone propionate. The one or more agents may comprise an anti-inflammatory antibiotic, such as erythromycin, azithromycin, or clarithromycin. The one or more agents may comprise chemotherapeutic agents, and anti-proliferative agents.

Polypeptide Therapeutic Agents

In other related aspects, the therapeutic agent includes an isolated peptide that modulates a target. For example, in one embodiment, the peptide of the invention inhibits or activates a target directly by binding to the target thereby modulating the normal functional activity of the target. In another embodiment, the peptide of the invention modulates the target by competing with endogenous proteins. In yet another embodiment, the peptide of the invention modulates the activity of the target by acting as a transdominant negative mutant.

The variants of the polypeptide therapeutic agents may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the polypeptide is an alternative splice variant of the polypeptide of the present invention, (iv) fragments of the polypeptides and/or (v) one in which the polypeptide is fused with another polypeptide, such as a leader or secretory sequence or a sequence which is employed for purification (for example, His-tag) or for detection (for example, Sv5 epitope tag). The fragments include polypeptides generated via proteolytic cleavage (including multi-site proteolysis) of an original sequence. Variants may be post-translationally, or chemically modified. Such variants are deemed to be within the scope of those skilled in the art from the teaching herein.

Pharmaceutical Compositions

The present invention provides pharmaceutical compositions comprising one or more tissue-targeting peptide of the present invention. The relative amounts of the tissue-targeting peptide, the pharmaceutically acceptable carrier, and any additional ingredients in a pharmaceutical composition of the invention will vary, depending upon the identity, size, and condition of the subject treated and further depending upon the route by which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit. Said compositions may comprise additional medicinal agents, pharmaceutical agents, carriers, buffers, adjuvants, dispersing agents, diluents, and the like depending on the intended use and application.

Examples of suitable pharmaceutical carriers, excipients and/or diluents are well known in the art and include, but are not limited to, a gum, a starch (e g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

Pharmaceutically acceptable carriers for liquid formulations are aqueous or non-aqueous solutions, suspensions, emulsions or oils, Non-limiting examples of non-aqueous solvents are propylene glycol, polyethylene glycol, and injectable organic esters such as ethyl oleate. Non-limiting examples of oils are those of animal, vegetable, or synthetic origin, for example, peanut oil, soybean oil, olive oil, sunflower oil, turmeric oil, fish-liver oil, another marine oil, or a lipid from milk or eggs.

Aqueous carriers include water, alcoholic/aqueous solutions, emulsions or suspensions, including saline and buffered media such as phosphate buffered saline solutions, water, emulsions, such as oil/water emulsions, various types of wetting agents, sterile solutions etc. Compositions comprising such carriers can be formulated by well-known conventional methods. Suitable carriers may comprise any material which, when combined with the biologically active compound of the invention, retains the biological activity. Preparations for parenteral administration may include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles may include sodium chloride solution, Ringer's dextrose, dextrose and sodium chloride, lactated Ringer's, or fixed oils. Intravenous vehicles may include fluid and nutrient replenishes, electrolyte replenishers (such as those based on Ringer's dextrose), and the like. Preservatives and other additives may also be present including, for example, antimicrobials, anti-oxidants, chelating agents, and inert gases and the like, in addition, the pharmaceutical composition of the present invention might comprise proteinaceous carriers, e.g., serum albumin or immunoglobulin, preferably of human origin.

A peptide-targeted composition may be administered alone, or in combination with other drugs and/or agents as pharmaceutical compositions. The composition may contain one or more added materials such as carriers and/or excipients. As used herein, "carriers" and "excipients" generally refer to substantially inert, non-toxic materials that do not deleteriously interact with other components of the composition. These materials may be used to increase the amount of solids in particulate pharmaceutical compositions, such as to form a powder of drug particles. Examples of suitable carriers include water, silicone, gelatin, waxes, and the like.

Examples of normally employed "excipients," include pharmaceutical grades of mannitol, sorbitol, inositol, dextrose, sucrose, lactose, trehalose, dextran, starch, cellulose, sodium or calcium phosphates, calcium sulfate, citric acid, tartaric acid, glycine, high molecular weight polyethylene glycols (PEG), and the like and combinations thereof. In one embodiment, the excipient may also include a charged lipid and/or detergent in the pharmaceutical compositions. Suitable charged lipids include, without limitation, phosphatidylcholines (lecithin), and the like. Detergents will typically be a nonionic, anionic, cationic or amphoteric surfactant. Examples of suitable surfactants include, for example, Tergitol® and Triton® surfactants (Union Carbide Chemicals and Plastics, Danbury, Conn.), polyoxyethylenesorbitans, for example, TWEEN surfactants (Atlas Chemical Industries, Wilmington, Del.), polyoxyethylene ethers, for example, Brij®, pharmaceutically acceptable fatty acid esters, for example, lauryl sulfate and salts thereof (SDS), and the like. Such materials may be used as stabilizers and/or anti-oxidants. Additionally, they may be used to reduce local irritation at the site of administration.

In at least one embodiment, the composition is formulated in a lyophilized form. In certain embodiments, the lyophilized formulation of the composition allows for maintaining the tissue-targeting peptide structure and achieving remarkably superior long-term stability conditions which might occur during storage or transportation of the tissue-targeting peptide.

Although the description of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions that are useful in the methods of the invention may be prepared, packaged, or sold in formulations suitable for ophthalmic, oral, rectal, vaginal, parenteral, topical, pulmonary, intranasal, buccal, or another route of administration. Other contemplated formulations include projected nanoparticles, liposomal preparations, resealed erythrocytes containing the active ingredient, and immunologically-based formulations.

The peptides and constructs of the invention may be converted into pharmaceutical salts by reacting with inorganic acids such as hydrochloric acid, sulfuric acid, hydrobromic acid, phosphoric acid, etc., or organic acids such as formic acid, acetic acid, propionic acid, glycolic acid, lactic acid, pyruvic acid, oxalic acid, succinic acid, malic acid, tartaric acid, citric acid, benzoic acid, salicylic acid, benezenesulfonic acid, and toluenesulfonic acids.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

The methods of the invention also encompass the use of pharmaceutical compositions comprising tissue-targeting peptide of the invention to practice the methods of the invention. The pharmaceutical compositions useful for practicing the invention may be administered to deliver a dose of from 100 ng/kg/day to 100 mg/kg/day. In one embodiment, the invention envisions administration of a dose which results in a concentration of the compound of the present invention from 1 µM to 10 µM in a mammal.

Typically, dosages which may be administered in a method of the invention to a mammal, preferably a human, range in amount from 0.5 µg to about 50 mg per kilogram of body weight of the mammal. The precise dosage administered will vary depending upon any number of factors, including but not limited to, the type of mammal and type of disease state being treated, the age of the mammal and the route of administration. Preferably, the dosage of the compound will vary from about 1 µg to about 10 mg per kilogram of body weight of the mammal. More preferably, the dosage will vary from about 3 µg to about 1 mg per kilogram of body weight of the mammal.

The compound may be administered to a mammal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the mammal, etc.

Routes of administration of any of the compositions of the invention include oral, nasal, rectal, parenteral, sublingual, transdermal, transmucosal (e.g., sublingual, lingual, (trans) buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

For oral application, particularly suitable are tablets, dragees, liquids, drops, suppositories, or capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and U.S. Pat. No. 4,265,874 to form osmotically controlled release tablets. Tablets may further comprise a sweetening agent, a flavoring agent, a coloring agent, a preservative, or some combination of these in order to provide for pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

For oral administration, the compositions of the invention may be in the form of tablets or capsules prepared by conventional means with pharmaceutically acceptable excipients such as binding agents; fillers; lubricants; disintegrates; or wetting agents. If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400).

Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid). Liquid formulations of a pharmaceutical composition of the invention which are suitable for oral administration may be prepared, packaged, and sold either in liquid form or in the form of a dry product intended for reconstitution with water or another suitable vehicle prior to use.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds of the invention, and a further layer providing for the immediate release of a medication for treatment of a disease. Using a wax/pH-sensitive polymer mix, a gastric insoluble composition may be obtained in which the active ingredient is entrapped, ensuring its delayed release.

Methods of Peptide-Targeted Delivery

The present invention also relates in part to methods of delivering an agent to a biological tissue. In various aspects of the invention, the methods comprise administering the compositions of the present invention to a subject in need thereof. In one embodiment, the composition comprises an agent and at least one peptide. In one embodiment, the peptide is a tissue-targeting peptide selectively targeting a biological tissue. In one embodiment, the peptide comprises the amino acid sequence of CKPFDRALC (SEQ ID NO: 1). In one embodiment, the peptide is conjugated to an agent. In one embodiment, the peptide is conjugated to a liposome. In one embodiment, the peptide is conjugated to a lipid. In one embodiment, the peptide is conjugated to a pharmaceutically acceptable carrier. In various embodiments, the peptide is conjugated to at least one agent, liposome, lipid, pharmaceutically acceptable carrier, or any combination thereof. In one embodiment, the peptide is reversibly bound to an agent. In one embodiment, the peptide is bound to a liposome. In one embodiment, the peptide is reversibly bound to a lipid. In one embodiment, the peptide is reversibly bound to a pharmaceutically acceptable carrier. In various embodiments, the peptide is reversibly bound to at least one agent, liposome, lipid, pharmaceutically acceptable carrier, or any combination thereof. In various embodiments, the agent is a therapeutic agent, prophylactic agent, diagnostic agent, imaging agent, contrast agent, microparticle, nanoparticle, or any combination thereof.

The present invention also relates in part to methods of treating a disease or disorder in a subject by delivery of an agent to a biological tissue of a subject. In various embodiments, the methods comprise administering the compositions of the present invention to a subject in need thereof. In one embodiment, the composition comprises at least one peptide and at least one agent. In one embodiment, the composition comprises at least one peptide and at least one liposome. In one embodiment, the composition comprises at least one peptide and at least one lipid. In one embodiment, the composition comprises at least one peptide and at least one pharmaceutically acceptable carrier. In various embodiments, the composition comprises at least one peptide and at least one agent, liposome, lipid, pharmaceutically acceptable carrier, or any combination thereof. In one embodiment, the peptide comprises the amino acid sequence of CKPFDRALC (SEQ ID NO: 1). In various embodiments, the peptide is conjugated to at least one agent, liposome, lipid, pharmaceutically acceptable carrier, or any combination thereof.

In various embodiments, the agent is a protein, peptide, peptidomimetic, antibody, ribozyme, vector, nucleic acid molecule, antisense nucleic acid, small molecule drug, organic compound, inorganic compound, or any combination thereof. In various embodiments, the agent is a therapeutic agent, prophylactic agent, diagnostic agent, imaging agent, contrast agent, microparticle, nanoparticle, or any combination thereof. In one embodiment, the therapeutic agent is glucocorticoid. In one embodiment, the therapeutic agent is a biologic. In one embodiment, the therapeutic agent is an anti-arthritis drug. In various embodiments, the therapeutic agent is a glucocorticoid, biologic, anti-arthritis drug, or any combination thereof.

In one embodiment, the method comprises an intravenous administration. In one embodiment, the method comprises an oral administration. In one embodiment, the method comprises an aerosol administration. In one embodiment, the method comprises a parenteral administration. In one embodiment, the method comprises an ophthalmic administration. In one embodiment, the method comprises a pulmonary administration. In one embodiment, the method comprises a topical administration. In various embodiments, the method comprises at least one selected from the group consisting of an intravenous, oral, aerosol, parenteral, ophthalmic, pulmonary, and topical administration. In various embodiments, the method includes, but is not limited to pharmacotherapy, surgery, radiation, and chemotherapy. In one embodiment, the method further comprises administering adjuvant radiotherapy to the subject in need thereof.

In one embodiment, the disease or disorder is an immune-mediated disease. In one embodiment, the disease or disorder is an autoimmune disease. In one embodiment, the disease or disorder is an inflammatory disease. In one embodiment, the disease or disorder is an autoinflammatory disease. In one embodiment, the disease or disorder is a cancer. In various embodiments, the disease or disorder is an immune-mediated disease, autoimmune disease, inflammatory disease, autoinflammatory disease, cancer, or any combination thereof.

The following are non-limiting examples of inflammatory disorders that can be diagnosed, imaged, or treated by the disclosed methods and compositions: an acne vulgaris, asthma, atherosclerosis, celiac disease, chronic prostatitis, colitis, diverticulitis, glomerulonephritis, hidradenitis suppurativa, hypersensitivity, inflammatory bowel diseases, interstitial cystitis, lichen planus, mast cell activation syndrome, mastocytosis, myopathies, otitis, pelvic inflammatory disease, reperfusion injury, rheumatic fever, rheumatoid arthritis, osteoarthritis, spondyloarthritis and other spondyloarthropathies, rhinitis, sarcoidosis, transplant rejection, vasculitis, retinopathies involving neovascularization (such as age-related macular degeneration and diabetic retinopathy) or any combination thereof.

The following are non-limiting examples of immune-mediated diseases or disorders that can be diagnosed, imaged, or treated by the disclosed methods and compositions: an allergy, asthma, diabetes mellitus type 1, Graves' disease, leukocyte defects, multiple sclerosis, myopathies, psoriasis, rheumatoid arthritis, systemic lupus erythematosus, vasculitis, or any combination thereof.

The following are non-limiting examples of cancers that can be diagnosed, imaged, and/or treated by the disclosed methods and compositions: acute lymphoblastic; acute myeloid leukemia; adrenocortical carcinoma; adrenocortical carcinoma, childhood; appendix cancer; basal cell carcinoma; bile duct cancer, extrahepatic; bladder cancer; bone cancer; osteosarcoma and malignant fibrous histiocytoma; liposarcoma and anaplastic liposarcoma; brain stem glioma, childhood; brain tumor, adult; brain tumor, brain stem glioma, childhood; brain tumor, central nervous system atypical teratoid/rhabdoid tumor, childhood; central nervous system embryonal tumors; cerebellar astrocytoma; cerebral astrocytoma/malignant glioma; craniopharyngioma; ependymoblastoma; ependymoma; medulloblastoma; medulloepithelioma; pineal parenchymal tumors of intermediate differentiation; supratentorial primitive neuroectodermal tumors and pineoblastoma; visual pathway and hypothalamic glioma; brain and spinal cord tumors; breast cancer; bronchial tumors; Burkitt lymphoma; carcinoid tumor; carcinoid tumor, gastrointestinal; central nervous system atypical teratoid/rhabdoid tumor; central nervous system embryonal tumors; central nervous system lymphoma; cerebellar astrocytoma cerebral astrocytoma/malignant glioma, childhood; cervical cancer; chordoma, childhood; chronic lymphocytic leukemia; chronic myelogenous leukemia; chronic myeloproliferative disorders; colon cancer; colorectal cancer; craniopharyngioma; cutaneous T-cell lymphoma; esophageal cancer; Ewing family of tumors; extragonadal germ cell tumor; extrahepatic bile duct cancer; eye cancer, intraocular melanoma; eye cancer, retinoblastoma; biliary tract cancer, cholangiocarcinoma, anal cancer, neuroendocrine tumors, small bowel cancer, gallbladder cancer; gastric (stomach) cancer; gastrointestinal carcinoid tumor; gastrointestinal stromal tumor (gist); germ cell tumor, extracranial; germ cell tumor, extragonadal; germ cell tumor, ovarian; gestational trophoblastic tumor; glioma; glioma, childhood brain stem; glioma, childhood cerebral astrocytoma; glioma, childhood visual pathway and hypothalamic; hairy cell leukemia; head and neck cancer; hepatocellular (liver) cancer; histiocytosis, Langerhans' cell; Hodgkin lymphoma; hypopharyngeal cancer; hypothalamic and visual pathway glioma; intraocular melanoma; islet cell tumors; kidney (renal cell) cancer; Langerhans cell histiocytosis; laryngeal cancer; leukemia, acute lymphoblastic; leukemia, acute myeloid; leukemia, chronic lymphocytic; leukemia, chronic myelogenous; leukemia, hairy cell; lip and oral cavity cancer; liver cancer; lung cancer, non-small cell; lung cancer, small cell; lymphoma, aids-related; lymphoma, Burkitt; lymphoma, cutaneous T-cell; lymphoma, non-Hodgkin lymphoma; lymphoma, primary central nervous system; macroglobulinemia, Waldenstrom; malignant fibrous histiocytoma of bone and osteosarcoma; medulloblastoma; melanoma; melanoma, intraocular (eye); Merkel cell carcinoma; mesothelioma; metastatic squamous neck cancer with occult primary; mouth cancer; multiple endocrine neoplasia syndrome, (childhood); multiple myeloma/plasma cell neoplasm; mycosis; fungoides; myelodysplastic syndromes; myelodysplastic/myeloproliferative diseases; myelogenous leukemia, chronic; myeloid leukemia, adult acute; myeloid leukemia, childhood acute; myeloma, multiple; myeloproliferative disorders, chronic; nasal cavity and paranasal sinus cancer; nasopharyngeal cancer; neuroblastoma; non-small cell lung cancer; oral cancer; oral cavity cancer; oropharyngeal cancer; osteosarcoma and malignant fibrous histiocytoma of bone; ovarian cancer; ovarian epithelial cancer; ovarian germ cell tumor; ovarian low malignant potential tumor; pancreatic cancer, islet cell tumors; papillomatosis; parathyroid cancer; penile cancer; pharyngeal cancer; pheochromocytoma; pineal parenchymal tumors of intermediate differentiation; pineoblastoma and supratentorial primitive neuroectodermal tumors; pituitary tumor; plasma cell neoplasm/multiple myeloma; pleuropulmonary blastoma; primary central nervous system lymphoma; prostate cancer; rectal cancer; renal cell (kidney) cancer; renal pelvis and ureter, transitional cell cancer; respiratory tract carcinoma involving the nut gene on chromosome 15; retinoblastoma; rhabdomyosarcoma; salivary gland cancer; sarcoma, Ewing family of tumors; sarcoma, Kaposi; sarcoma, soft tissue; sarcoma, uterine; Sezary syndrome; skin cancer (nonmelanoma); skin cancer (melanoma); skin carcinoma, Merkel cell; small cell lung cancer;

small intestine cancer; soft tissue sarcoma; squamous cell carcinoma, squamous neck cancer with occult primary, metastatic; stomach (gastric) cancer; supratentorial primitive neuroectodermal tumors; T-cell lymphoma, cutaneous; testicular cancer; throat cancer; thymoma and thymic carcinoma; thyroid cancer; transitional cell cancer of the renal pelvis and ureter; trophoblastic tumor, gestational; urethral cancer; uterine cancer, endometrial; uterine sarcoma; vaginal cancer; vulvar cancer; Waldenstrom macroglobulinemia; Wilms tumor, neovascularized tumors, and any combination thereof.

In another aspect, the invention relates to methods of diagnosing a disease or disorder in a subject by delivery of an agent to a biological tissue of a subject. In various embodiments, the methods comprise administering the compositions of the present invention to a subject in need thereof. In various embodiments, the composition comprises at least one peptide and at least one agent, liposome, lipid, pharmaceutically acceptable carrier, or any combination thereof. In one embodiment, the peptide comprises the amino acid sequence of CKPFDRALC (SEQ ID NO: 1).

In another aspect, the invention also relates to methods of imaging a disease or disorder in a subject by delivery of an agent to a biological tissue of a subject. In various embodiments, the methods comprise administering the compositions of the present invention to a subject in need thereof. In various embodiments, the composition comprises at least one peptide and at least one agent, liposome, lipid, pharmaceutically acceptable carrier, or any combination thereof. In one embodiment, the peptide comprises the amino acid sequence of CKPFDRALC (SEQ ID NO: 1).

The diseases and disorders to be treated, diagnosed, and/or imaged include any disease described herein, as will be understood by one of ordinary skill in the art. Such diseases and disorders include, but are not limited to, a disease or disorder involving neovascularization as described herein and/or as will be appreciated by the skilled artisan.

Kits of the Invention

The invention also includes a kit comprising compounds useful within the methods of the invention and an instructional material that describes, for instance, the method of administering the tissue-targeting peptides and compositions as described elsewhere herein. The kit may comprise formulations of a pharmaceutical composition comprising the active ingredient combined with a pharmaceutically acceptable carrier, such as sterile water or sterile isotonic saline. The kit may comprise injectable formulations that may be prepared, packaged, or sold in unit dosage form, such as in ampules or in multi dose containers containing a preservative. The kit may comprise formulations including, but not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a kit, the active ingredient is provided in dry (i.e., powder or granular) form for reconstitution with a suitable vehicle (e.g., sterile pyrogen free water) prior to administration of the reconstituted composition.

The kit may comprise pharmaceutical compositions prepared, packaged, or sold in the form of a sterile aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic diluent or solvent, such as water or 1,3 butane-diol, for example. Other acceptable diluents and solvents include, but are not limited to, Ringer's solution, isotonic sodium chloride solution, and fixed oils such as synthetic mono or di-glycerides. Other formulations which are useful include those which comprise the active ingredient in microcrystalline form, in a liposomal preparation, or as a component of a biodegradable polymer system.

In certain embodiments, the kit comprises instructional material. Instructional material may include a publication, a recording, a diagram, or any other medium of expression which can be used to communicate the usefulness of the device or implant kit described herein. The instructional material of the kit of the invention may, for example, be affixed to a package which contains one or more instruments which may be necessary for the desired procedure. Alternatively, the instructional material may be shipped separately from the package, or may be accessible electronically via a communications network, such as the Internet.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: Preparation and Characteristics of Liposomes

In the previous studies, a panel of phage-encoded peptides that home to inflamed joints of arthritic rats following intravenous injection and systemic circulation of a phage library was identified. In the process of bioinformatics analysis of these peptides, including random sequence variations and scrambling of potential motifs present in these peptides, a peptide sequence CKPFDRALC (SEQ ID NO: 1) (named as ART-2) was uncovered. ART-2 showed preferential homing to rat arthritic joints and avid binding to endothelial cells, which are vital for new blood vessel formation (angiogenesis); a characteristic feature of RA (Ezaki T et al., 2001, The American Journal of Pathology 158:2043-2055; Szekanecz Z et al., 2009, Vascular Pharmacology 51:1-7; Szmitko P E et al., 2003, Circulation 108: 1917-1923). As such, the present invention relates in part to the use of a peptide sequence CKPFDRALC (SEQ ID NO: 1) (named as ART-2) (FIG. 1A).

For peptide-displaying liposomes, ART-2-lipopeptide (FIG. 1B) was added to the lipids at 1 molar ratio. The solvent was removed using nitrogen gas and the dried lipid film was reconstituted with one milliliter (mL) of PBS (phosphate-buffered saline) or sterile deionized water and the mixture then set overnight at room temperature (RT) to swell. Vortexing the vial for 3 min at RT yielded multilamellar vesicles (MLVs). Thereafter, sequential sonication of MLVs using an ultrasonic water bath and a probe sonifier produced small unilamellar vesicles (SUVs). Subsequent centrifugation using an Amicon filter for 20 min at 5,000 rpm removed un-encapsulated dye.

Liposomes containing DEX were prepared using the procedure described above but with the following modifications: a) the dried lipid film was hydrated with DEX (150 µg) dissolved in 1 mL PBS; and b) to remove un-entrapped DEX, liposomes thus obtained were centrifuged for 20 min at 10,000 rpm employing an Amicon filter. After removing un-encapsulated DEX, then liposomes were reconstituted with PBS (Migliore M M et al., 2010, Journal of Pharmaceutical Sciences 99:1745-1761).

The liposomes were 95 to 106 nm in size, with DEX-containing liposomes ranging from 96-105 nm (FIG. 2A through FIG. 2D) compared with FITC-containing liposomes that measured 70-95 nm (FIG. 2E and FIG. 2F). The size of Cy7-containing liposomes was comparable to that of FITC-containing liposomes (data not shown.) For the two types of DEX liposomes, TEM imaging validated the morphology as well as size (FIG. 3A and FIG. 3B), whereas Zeta sizer assessed their charge (FIG. 3C and FIG. 3D). The efficiency of entrapment for the drug (DEX) was 73-78%, whereas that for the dye (FITC/Cy7) was about 100%. Furthermore, when stored at room temperature, the liposomes (DEX, FIG. 2C and FIG. 2D; FITC, FIG. 2E and FIG. 2F) were found to be stable for at least two weeks (Table 1).

The American Journal of Pathology 158:2043-2055; Szmitko P E et al., 2003, Circulation 108:1917-1923). Therefore, ligands that bind to endothelial cells are sought for modulation of their activity as well as drug delivery approaches targeting these cells. In this regard, ART-2 represents a promising ligand for endothelial cells. These attributes of ART-2 peptide are described below, along with its ability to direct liposomes encapsulating dexamethasone (DEX), a potent anti-arthritic drug, preferentially into inflamed joints. The present invention also shows that targeted delivery of DEX using ART-2 liposomes was superior to untargeted (control) liposomal delivery of DEX or free DEX in inhibiting arthritis progression in rats.

Figure 5:
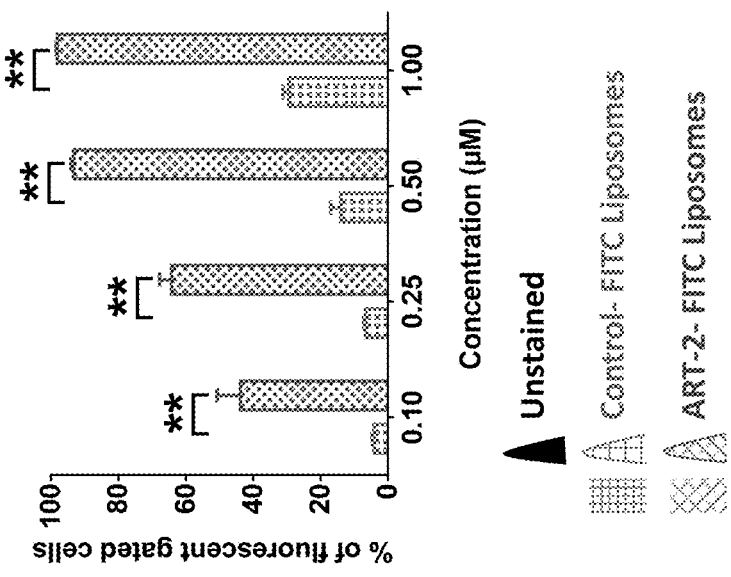
FIG. 5, comprising
Figure 5:
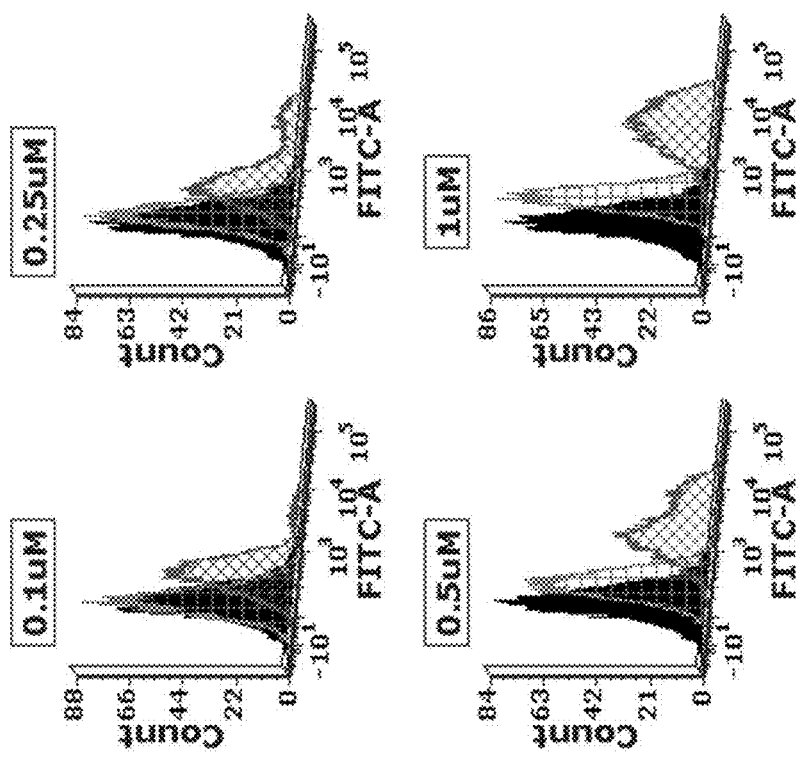

For this reason, the present invention also relates in part to the development of a peptide-directed liposomal drug delivery system for arthritis therapy that is based on the rat adjuvant-induced arthritis (AA) model of human RA. The binding of peptide ART-2 itself (not as part of liposomes) to endothelial cells (HUVEC) was described above (FIG. 4A and FIG. 4B). The same peptide but conjugated to a lipid (ART-2-lipopeptide) (FIG. 1B) was then used for preparing the test liposomes, while control liposomes lacked this peptide in order to assess whether conjugation of peptide ART-2 to lipids and/or the incorporation of the resulting lipopeptide into liposomes had any significant effect on the binding of peptide ART-2 to endothelial cells. It was evident from both the dose titration (FIG. 5A and FIG. 5B) and time kinetics (FIG. 5C and FIG. 5D) that ART-2-liposomes showed much higher endothelial cell-binding compared

TABLE 1

A summary of the liposomal size and polydispersity index (PDI) based on the data shown in FIG. 2C through FIG. 2E.

|  | Size (nm) | | PDI | |
| --- | --- | --- | --- | --- |
|  | Day 0 | Day 14 | Day 0 | Day 14 |
| ART-2-DEX-Liposomes | 96.136 ± 0.58 | 96.663 ± 0.55 | 0.298 ± 0.002 | 0.288 ± 0.002 |
| Control-DEX-Liposomes | 102.967 ± 0.809 | 105.167 ± 0.636 | 0.420 ± 0.003 | 0.371 ± 0.002 |
| ART-2-FITC-Liposomes | 70.653 ± 0.697 | 71.34 ± 0.142 | 0.268 ± 0.002 | 0.273 ± 0.005 |
| Control-FITC-Liposomes | 85.223 ± 0.125 | 95.94 ± 0.181 | 0.255 ± 0.004 | 0.253 ± 0.005 |

Figure 6:
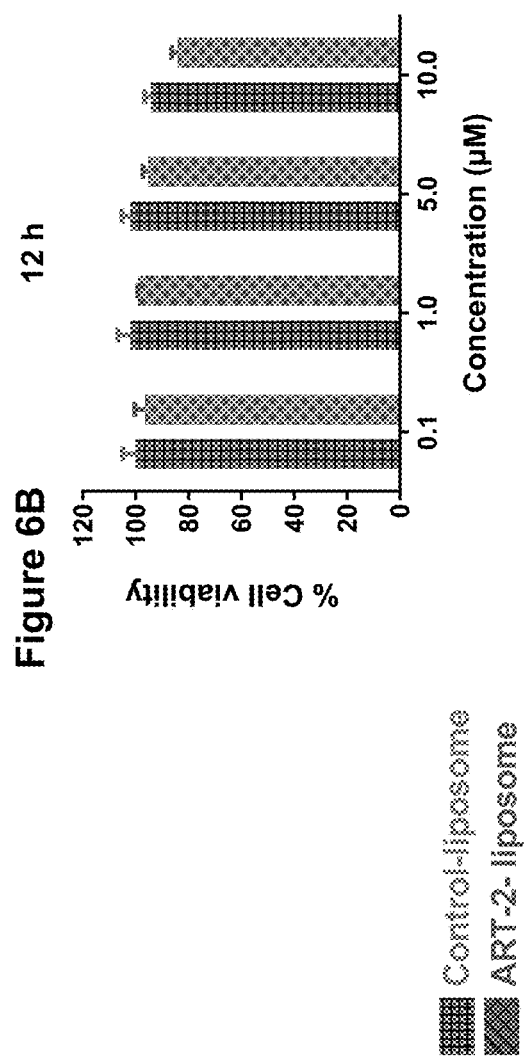
FIG. 6, comprising
Figure 6:
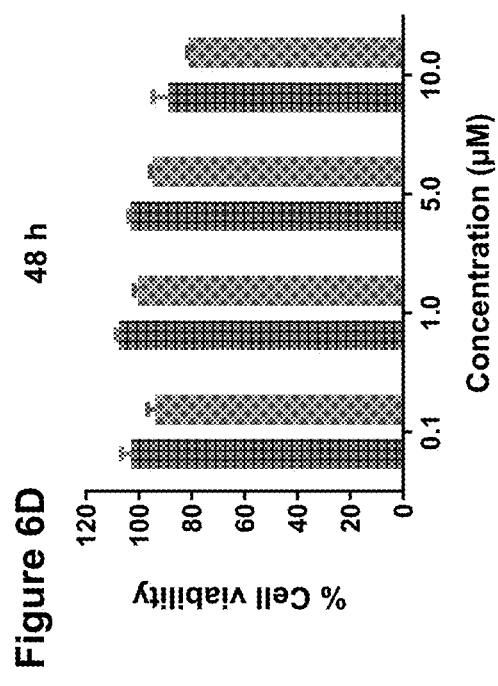
Figure 6:
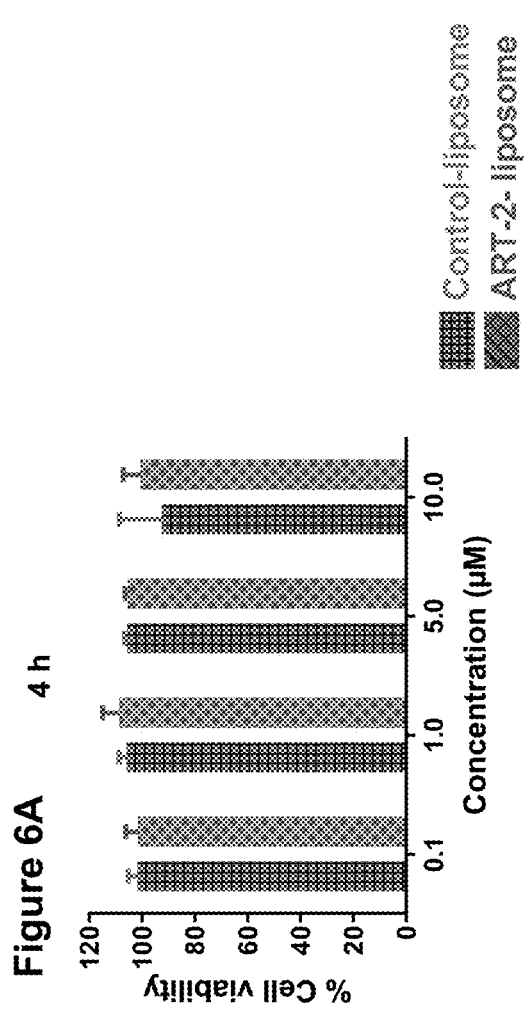
Figure 6:
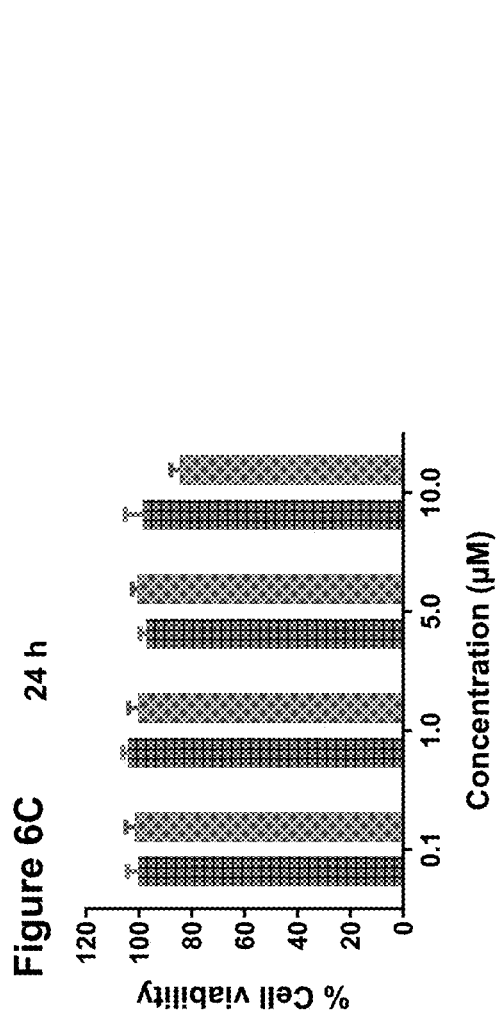

Example 2: The Display of ART-2 on Liposomes Enhanced Their Endothelial Cell-Binding Attribute As mentioned above, previous studies has identified a panel of phage-encoded peptides that home to inflamed joints of arthritic rats following intravenous injection and systemic circulation of a phage library was identified. In the process of bioinformatics analysis of these peptides, including random sequence variations and scrambling of potential motifs present in these peptides, a newly-uncovered peptide ART-2 showed not only preferential homing to rat arthritic joints, but also avid binding to endothelial cells (FIG. 4). Endothelial cells lining the blood vessels of the synovial tissue in the joints not only control the migration of leukocytes from blood circulation into the joint, but also are vital for new blood vessel formation (angiogenesis), which is a characteristic feature of RA (Ezaki T et al., 2001, The American Journal of Pathology 158:2043-2055; Szekanecz Z et al., 2009, Vascular Pharmacology 51:1-7; Szmitko P E et al., 2003, Circulation 108:1917-1923). Pro-inflammatory cytokines and other mediators of inflammation produced in the course of arthritis cause the activation and proliferation of endothelial cells, which in turn affect the processes of cellular migration and angiogenesis (Ezaki T et al., 2001, with that of control liposomes. Tests were also conducted to assess whether the drug delivery vehicles, namely the ART-2/Control liposomes, had any toxic effect on cells. For this purpose, the effect of these liposomes on HUVEC was tested using an MTT-based cell viability assay as described in the Method portion of the Experimental Examples section. The results (FIG. 6) showed a minimal toxic effect of the two liposomal preparations when tested on HUVEC for 4 to 48 h. At each of the liposomal concentrations tested, the cell viability of HUVEC ranged from about 80 to 100% (FIG. 6). The difference between the liposomal-treated cells and untreated cells was not statistically significant. Thus, the drug delivery vehicle was safe for in vitro and in vivo testing.

Figures 7, 7A:
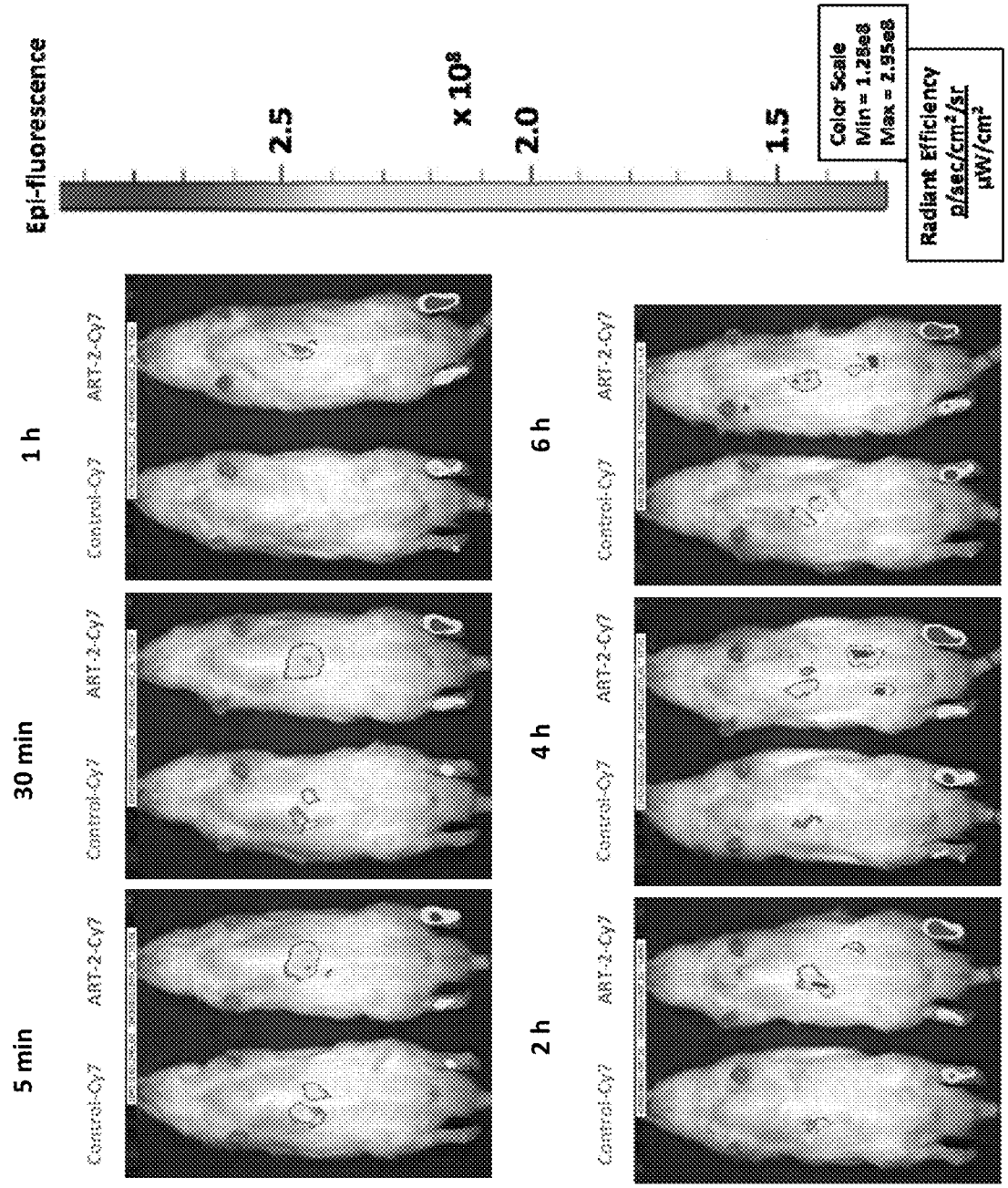

Example 3: Arthritis Joints Show High Concentration of Fluorescence Signal Following Intravenous Injection of Dye-Entrapping ART-2-Liposomes The fluorescence intensity in hind paws of arthritic rats after injecting intravenously (i.v.) ART-2-Cy7 liposomes versus control-Cy7 liposomes were also compared. The fluorescence signal in hind paws was much higher with ART-2-Cy7 liposomes than that with control-Cy7 liposomes at each of the time points tested (FIG. 7A). In the case of the former, a signal in the joints was detectable as early as 5 min after injection, which peaked at 4 h, followed by slightly reduced intensity at 6 h time point. Interestingly, the fluorescence signal was higher in the hind paw with more severe arthritis than in the opposite paw with less severe disease. At the termination of experiment at 6 h, fluorescence signal was detectable not only in the arthritic paws but also in the liver and kidney (FIG. 7B). Although not bound by any particular theory, the observed signal from these abdominal organs might be because of Cy7 clearance by these organs. However, under the same test conditions, hind paws of naïve rats showed no fluorescence signal (FIG. 7C). This assessment of the fluorescence signal is comparative among different paws and organs, and the results show an association between higher disease severity and higher fluorescence signal in arthritic rats.

Example 3: Peptide-Targeted Liposomal Delivery of Dexamethasone for Arthritis Therapy ART-2-Targeted Liposomal DEX was More Effective in Suppressing Arthritis in Rats than Untargeted Liposomal DEX or Free DEX Three different treatment modalities based on DEX were tested for their relative efficacy in suppressing arthritis in rats. These modalities included two liposomal forms of DEX and free DEX. An equal amount of DEX was delivered via different treatment modalities. ART-2-DEX liposomes were more efficacious in inhibiting AA than either control-DEX liposomes or free DEX (FIG. 8A and FIG. 8B). On the other hand, control-DEX liposomes showed a similar level of anti-arthritic effect as free DEX, when both were compared with vehicle-treated controls. The differences in arthritic scores of ART-2-DEX versus control rats; ART-2-DEX versus control-DEX; and ART-2-DEX versus free DEX were statistically significant. The severity of clinical arthritis of various treatment groups of rats was further validated by histological examination of hind paw sections (FIG. 8C).

DEX Delivered Via Liposomes Showed a Similar Profile of Systemic Adverse Effects as DEX Given Via Plain (Control) Liposomes or without Liposomes (Free DEX)

Figure 9:
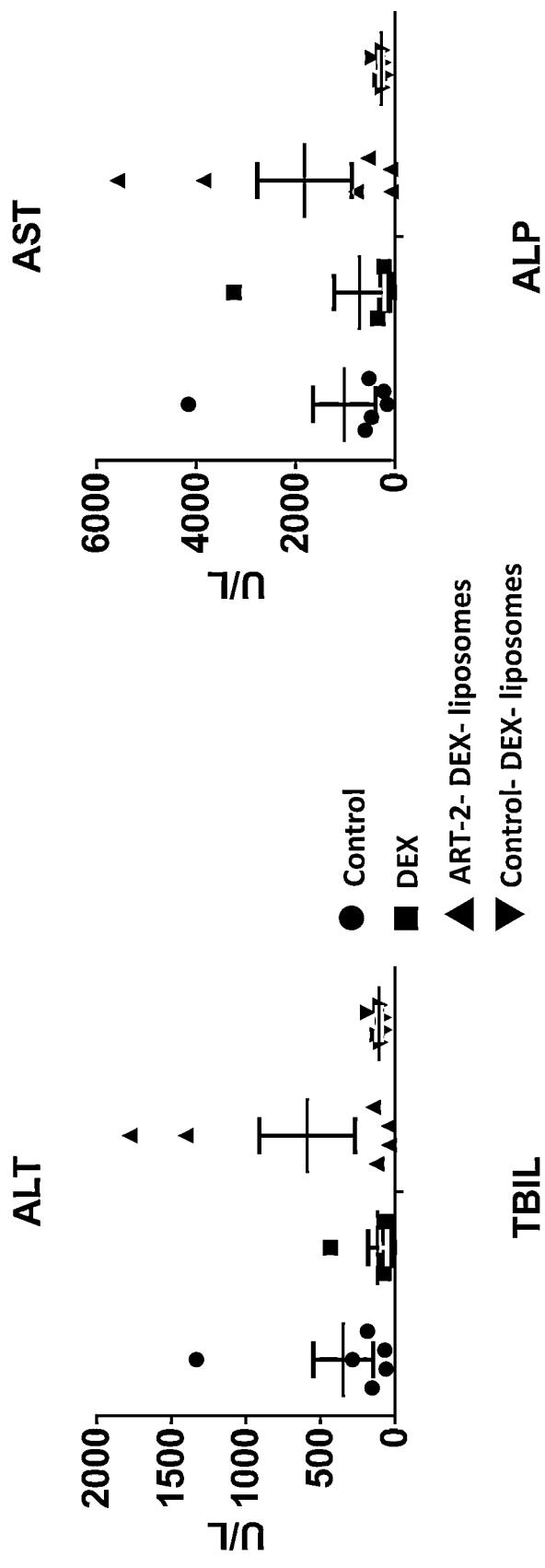
FIG. 9, comprising
Figure 9:

The sera of rats treated with DEX delivered in different forms (liposomes or free) were tested for any effects on the liver and biliary system, pancreas, and kidneys, as well as general tissue damage. The serum chemistry profile of the 3 groups of treated rats was comparable to each other, as well as to that of untreated arthritic controls (FIG. 9). Taken together, the results of arthritis-inhibitory effects (FIG. 8) and serum chemistry analysis, the latter serving as an indirect pointer to systemic toxicity effects (FIG. 9), revealed that the highest therapeutic index of DEX was achieved via targeted delivery using ART-2-DEX liposomes than that with other drug delivery approaches tested.

Despite the availability of potent anti-arthritic drugs for the treatment of RA, there is limitation imposed by the potential risk of adverse effects involving other organs such as the liver and the kidney (Gibofsky A, 2014, Am J Manag Care 20:S136-144; Curtis J R et al., 2011, Clin Ther 33:679-707; Kim G W et al., 2015, Arch Pharm Res 38:575-584; Bui V L et al., 2018, Clinical Immunology; Sfikakis P P et al., 2011, Clinical Immunology 141:231-235). For the newer class of drugs, the biologics (e.g., anti-TNF-α), a risk of severe infections is a concern (Sfikakis P P et al., 2011, Clinical Immunology 141:231-235; Ramiro S et al., 2017, Annals of the Rheumatic Diseases 76:1101-1136). One of the factors contributing to some of the adverse effects is the unavoidable exposure of healthy organs to the systemically administered drugs, whose primary target otherwise is the inflamed joint. Thus, novel ways to improve the benefit/risk ratio (or therapeutic index) of these drugs are being sought. These include, but are not limited to, the use of different types of nanoparticles (Allen T M et al., 2013, Advanced Drug Delivery Reviews 65:36-48; Koning G A et al., 2006, Arthritis and Rheumatism 54:1198-1208; Ruoslahti E et al., 2010, The Journal of Cell Biology 188:759-768; Sercombe L et al., 2015, Frontiers in Pharmacology 6:286; Yang M et al., 2017, Journal of Controlled Release 252:108-124) and drug-polymer/folate conjugates (Yang M et al., 2017, Journal of Controlled Release 252:108-124; Ferrari M et al., 2015, Nature Reviews 11:328-337; Qi R et al., 2015, Journal of Biomedical Nanotechnology 11:1431-1441; Yang M et al., 2018, Nanomedicine: Nanotechnology, Biology and Medicine 14:1815-1816). The baseline parameters under consideration here are the dose of a drug and its systemic adverse effects. Therefore, therapeutic index of a drug can be improved by: a) increasing its efficacy for a given dose and reducing its adverse effects; b) increasing efficacy at the same dose but without affecting the extent of adverse effects; c) maintaining efficacy at the same dose but reducing adverse effects; and d) maintaining efficacy at a reduced dose but without affecting the extent of adverse effects. This invention, in part, describes a peptide-directed liposomal drug delivery method to improve the therapeutic index of DEX, which represents a widely used class of drugs for RA therapy. It was achieved via mechanism 'b' above, i.e., by increasing efficacy at the same dose but without affecting adverse effects.

Targeted drug delivery aimed at a particular organ requires a suitable ligand that can direct the nanoparticle carrying that drug to that tissue. In the system of the present invention, a novel peptide ART-2 was used to achieve this objective. Liposomes were used as carriers of DEX, and these liposomes displayed peptide ART-2 on their surface along with polyethylene glycol (PEG). The latter reduces the clearance of liposomes by the reticuloendothelial system of the liver. Control-DEX liposomes had all the same ingredients except peptide ART-2. The test/control liposomes were within the expected range of size (nm). The ART-2-DEX liposomes had a slightly different net charge than control liposomes, and although not bound by any particular theory, this difference could be because of the ART-2 peptide displayed on the test liposomes. For an objective comparison, for in vivo treatment of arthritis in rats, an equal dose of DEX (amount per Kg body weight), either in the form of liposomes or as free drug, was administered intravenously to rats. It is clear from these results that the peptide-targeted liposomal DEX had a significantly higher inhibitory effect on arthritis progression than non-targeted liposomes or free DEX.

As discussed above, another parameter for assessment of therapeutic index is the extent of adverse reactions. In these studies, serum chemistry of known enzymes/markers that are associated with physiological functions and tissue pathology of different organ systems (e.g., liver function, kidney function, pancreatic function, general tissue toxicity, etc.) was employed. The results showed that despite increasing the efficacy of the anti-arthritic activity of DEX by ART-2-DEX liposomes, there was no additional increase in the enzymes/markers of tissue pathology when compared with that of control liposomes or free DEX. In view of different treatment categories mentioned above, ART-2-

DEX liposomes had an improved therapeutic index via mechanism 'b' (enhanced efficacy but without increasing the adverse effects).

Many of the previous studies focused toward drug deliver for arthritis therapy used only plain liposomes that lacked a ligand to direct those liposomes to arthritic joints, and therefore were not as effective for targeted and controlled drug delivery as the use of peptide ART-2 liposomes described in the present invention. For example, other investigators have reported liposomal delivery of anti-arthritic drugs such as prednisolone, betamethasone, DEX, and methotrexate (MTX) in animal models of RA, including collagen-induced arthritis (CIA) and AA (Anderson R et al., 2010, Arthritis Research & Therapy 12:R147; Hofkens W et al., 2011, Journal of Controlled Release 152:363-369; Prabhu P et al., 2012, International Journal of Nanomedicine 7:177-186; Van Den Hoven J M et al., 2011, International Journal of Pharmaceutics 416:471-477; Ulmansky R et al., 2012, Journal of Controlled Release 160:299-305). Plain liposomes were used in these studies. Another set of studies employed a peptide ligand to direct liposomes for arthritis therapy in the AA model (Koning G A et al., 2006, Arthritis and Rheumatism 54:1198-1208; Vanniasinghe A S et al., 2014, Clinical Immunology 151:43-54; Poh S et al., 2017, Nanomedicine 12:2441-2451), but that ligand was different from ART-2 peptide. For example, the following types of liposomes have been used for arthritis therapy in different studies: liposomes containing DEX and displaying a peptide with RGD motif on the surface (Koning G A et al., 2006, Arthritis and Rheumatism 54:1198-1208); liposomes encapsulating prednisolone and presenting on their surface a peptide ligand that has avidity for fibroblast-like synoviocytes (Vanniasinghe A S et al., 2014, Clinical Immunology 151:43-54); liposomes entrapping betamethasone but expressing folate on liposomal surface for imaging and therapeutic studies (Poh S et al., 2017, Nanomedicine 12:2441-2451); and liposomes expressing a peptide ligand for endothelial cells and containing within them IL-27, an immunomodulatory cytokine (Meka R R et al., 2018, Journal of Controlled Release 286:279-288; Meka R R et al., 2015, Autoimmunity Reviews 14:1131-1141). As such the present invention describes the use of a novel peptide ligand for targeted drug (DEX) delivery, which was not described before. In addition, the present invention also assessed adverse effects by measuring serum enzymes/markers, which was not done in many of the above-mentioned studies that were limited to measurement of arthritis inhibition alone. Furthermore, the present invention relates in part to the peptide ligand (ART-2) that showed binding to endothelial cells.

Another novel approach for drug delivery that has been described for arthritis involves conjugation of a cytokine (e.g., IL-4) (Wythe S E et al., 2013, Annals of the Rheumatic Diseases 72:129-135) or a drug (e.g., MTX) (Yang M et al., 2018, Nanomedicine: Nanotechnology, Biology and Medicine 14:1815-1816; Yang M et al., 2017, Theranostics 7:97-105) to a targeting ligand. For example, conjugation of TL-4 to a peptide ligand (e.g., a synovial endothelium-targeting peptide CKSTHDRLC (SEQ ID NO: 2)) was shown to be highly effective when tested in the synovial xenograft model of RA (Wythe S E et al., 2013, Annals of the Rheumatic Diseases 72: 129-135). Similarly, MTX conjugated to dextran sulfate was shown to have a marked anti-arthritic effect against CIA in mice (Yang M et al., 2018, Nanomedicine: Nanotechnology, Biology and Medicine 14:1815-1816; Yang M et al., 2017, Theranostics 7:97-105). One of these MTX-based formulations targeted the scavenger receptor on activated macrophages (Yang M et al., 2017, Theranostics 7:97-105). The present invention also relates in part to an approach of directly conjugating MTX to a joint-homing peptide ligand for treatment of arthritis in the AA model was found to be more effective compared to the use of free drug.

The application of targeted drug delivery is advancing rapidly in the field of autoimmune diseases. Besides its use for arthritis therapy summarized above, liposomal drug delivery has also been used for therapy in animal models of experimental autoimmune uveoretinitis (Zhang R et al., 2017, The British Journal of Ophthalmology), experimental autoimmune encephalomyelitis (EAE), (Turjeman K et al., 2015, PloS One 10:e0130442; Fuhrmann T et al., 2015, Neuroscience Letters 602:126-132; Gammon J M et al., 2015, Journal of Controlled Release 210:169-178); and SLE (or lupus) (Look M et al., 2013, The Journal of Clinical Investigation 123:1741-1749; Scindia Y et al., 2008, Arthritis and Rheumatism 58:3884-3891). Besides the use of peptides and folate described above, antibodies (e.g., anti-8 integrin or anti-CD4 antibody) (Look M et al., 2013, The Journal of Clinical Investigation 123:1741-1749; Scindia Y et al., 2008, Arthritis and Rheumatism 58:3884-3891) and glutathione (Gaillard P J et al., 2012, Journal of Controlled Release 164:364-369) have also been employed as ligands for drug delivery in above studies.

The materials and methods are now described.

Materials and Methods

Preparation and Characterization of Liposomes

Materials

Cholesterol, DEX (dexamethasone), DOPC (1,2-Dioleoyl-s n-glycero-3-phosphocholine), DOPE (1,2-Dioleoyl-sn-glycero-3-phosphoethanolamine), and FITC (fluorescein isothiocyanate) were obtained from Sigma-Aldrich, USA, whereas DSPE-PEG (2000) amine (ammonium salt of 1,2-distearoyl-sn-glycero-3-phosphoethanolamine-N-[amino (polyethylene glycol)-2000]) was from Avanti Polar Lipids, USA. Cy7 (Cyanine 7 azide) was from Lumiprobe, USA. ART-2 peptide (CKPFDRALC) (SEQ ID NO: 1) (FIG. 1A) labeled with FITC or Cy7, and ART-2-lipopeptide (CK-PFDRALC (SEQ ID NO: 1)-NH—$C_{18}H_{37}$) (FIG. 1B) were synthesized by GenScript/Lifetein, USA. The conjugation of peptide with octadecylamine was confirmed by Electrospray Ionisation-Mass Spectrometry (ESI-MS) (m/z calculated 1303.76 (for CKPFDRALC (SEQ ID NO: 1)-NH—$C_{18}H_{37}$), observed 1303.70[M+H]+ and 652.75[M+2H]2+) (FIG. 10A), whereas the purity of the ART-2-lipopeptide was confirmed by reverse phase (RP) analytical high performance liquid chromatography (HPLC) (FIG. 10B).

Liposomes Containing a Dye (FITC/Cy7) or Drug (DEX)

For preparing liposomes, various lipids and a fluorescent dye were dissolved in chloroform/methanol in a glass vial in the following molar ratio: DOPC, 1; DOPE, 0.6; cholesterol 0.4; DSPE-(PEG)45-NH2), 0.05; and FITC/Cy7, 0.05. For control liposomes, only the lipids were used. For peptide-displaying liposomes, ART-2-lipopeptide (FIG. 1B) was added to the lipids at 1 molar ratio. The solvent was removed using nitrogen gas and the dried lipid film was reconstituted with one milliliter (mL) of PBS (phosphate-buffered saline) or sterile deionized water and the mixture then set overnight at room temperature (RT) to swell. Vortexing the vial for 3 min at RT yielded multi-lamellar vesicles (MLVs). Thereafter, sequential sonication of MLVs using an ultrasonic water bath and a probe sonifier produced small unilamellar vesicles (SUVs). Subsequent centrifugation using an Amicon filter for 20 min at 5,000 rpm removed un-encapsulated dye.

Liposomes containing DEX were prepared using the procedure described above but with the following modifications: a) the dried lipid film was hydrated with DEX (150 µg) dissolved in 1 mL PBS; and b) to remove un-entrapped DEX, liposomes thus obtained were centrifuged for 20 min at 10,000 rpm employing an Amicon filter. After removing un-encapsulated DEX, then liposomes were reconstituted with PBS (Migliore M M et al., 2010, Journal of Pharmaceutical Sciences 99:1745-1761).

Imaging of Liposomes Using Transmission Electron Microscope (TEM) FEI Tecnai T12

Liposomes (5 µL) were placed on a copper grid (200-mesh size). Any excess sample was removed and 5 µL of a 2% solution (w/v) of uranyl acetate were added. Five min later, the sample was air dried at RT. Thereafter, TEM imaging of liposomes was performed (Helmy H S et al., 2017, International Journal of Nanomedicine 12:7015-7023).

Zatasizer-Based Determination of Liposomal Size, Potential, and Stability

Using a Zetasizer (Malvern Zetasizer Nano), the size of liposomes (in 50 µL sample) was measured in 1 mL deionized water. The particle size was measured 10 times in triplicate using dynamic light scattering (DLS) and applying zero field correction. Similarly, zeta potential was measured 10 times by assessing the viscosity, 0.89 cP; dielectric constant, 79; and temperature, 25° C., and then Smoluchowski approximation was used to derive the average value (Rakeshchandra R et al., 2016, RSC Advances 6:77841-77848). To assess the stability of liposomes, FITC-/DEX-containing liposomes were prepared and then stored at RT. The size and polydispersity index (PDI) of liposomes were measured on day 0 and then 14 days later.

HPLC Measurement of Loading of DEX into Liposomes

After centrifugation of the DEX-containing liposomes, the un-entrapped DEX was collected and analyzed by RP-HPLC (Waters Inc.) and a photodiode detector. (For HPLC, the ratio of water:acetonitrile:methanol was 50:25:25 (v:v:v) ratio and the flow rate was 0.1 mL/min at 25° C.) After subtracting the amount of un-entrapped DEX from total DEX used, the amount of entrapped DEX was derived and presented as a percent of total.

Testing the Endothelial Cell-Binding of Liposomes In Vitro

HUVEC (human umbilical vein endothelial cell) (ATCC, Manassas, Va., USA) line was grown in a special medium, endothelial cell basal medium (Lonza, USA) supplemented with fetal bovine serum (10%). The cells were cultured at 37° C. in a 12-well plate at a density of $2 \times 10^5$ cells/well in 5% $CO_2$ and 95% air. After 18-24 h, cells were stained for 2 h with different concentrations (0.1, 0.25, 0.5 µM and 1 µM) of liposomes, and then washed with PBS. The cells were then fixed for 15 min using 1% paraformaldehyde, and analyzed by Flow cytometry. For time kinetics study, the same procedure was followed using a single concentration (0.5 µM) of liposomes but incubated with cells for different time points (5, 30, 60 and 120 min). Data analysis was done using FCS Express 6.

Assessing the Cytotoxicity of the Drug Delivery Vehicle

The cytotoxicity of ART-2-/Control liposomes for HUVEC was assessed using an MTT (3-(4,5-dimethylthiazol-2-yl)-2,5-diphenyltetrazolium bromide)-based reduction assay (Meka R R et al., 2016, RSC Advances 6:77841-77848). The assay was performed in triplicates in a 96-well plate at a density of 10,000 cells per well. After 12 h of seeding the wells with HUVEC, the cells were treated with different concentrations of liposomes (0.1 µM-10 PM) and incubated for 4 h to 48 h. After that, MTT (0.05 mg/100 µL/well) was added to the cells and incubated for another 4 h at 37° C. Thereafter, the culture medium was replaced with 100 L/well of DMSO:MeOH (50:50) solution. The absorbance was measured at 570 nm using a BioRad microplate reader (CA, USA). Results were expressed as percent of cell viability=[A570 (treated cells)-background/A570 (untreated cells)-background]×100.

Induction and Evaluation of Adjuvant-Induced Arthritis (AA) in Lewis Rats

Five to 6 weeks old male Lewis (LEW/SsNHsd) rats obtained from Envigo (Indianapolis, Ind.) were used in this study. The handling of rats and experimental procedures were performed as per institutional guidelines for the care and use of animals. Water and food were accessible to rats ad libitum. The rats were kept at 21-23° C. at a light-dark cycle of 12 h. For arthritis induction, heat killed *Mycobacterium tuberculosis* H37Ra (Mtb) (Difco, Detroit, Mich.) suspended in mineral oil was injected subcutaneously (s.c.) into Lewis rats at the base of the tail (1.5 mg/rat) as described elsewhere (Yang Y H et al., 2011, Proceedings of the National Academy of Sciences of the USA 108:12857-12862; Rajaiah R et al., 2011, The Journal of Biological Chemistry 286:2817-2825). The rats were then observed regularly for signs of arthritis. The disease severity was evaluated on the basis of erythema and swelling of the paws. A grade from 0-4 per paw was assigned. After completing disease scoring, the hind paws were collected, decalcified, and processed for histological analysis (Astry B et al., 2015, Clinical Immunology 157:228-238; Moudgil K D et al., 1997, The Journal of Experimental Medicine 185:1307-1316; Venkatesha S H et al., 2011, The Journal of Biological Chemistry 286:15138-15146). Microscopic examination of the tissue sections was then performed to assess pannus growth, damage to cartilage, and bone erosion (Astry B et al., 2015, Clinical Immunology 157:228-238; Moudgil K D et al., 1997, The Journal of Experimental Medicine 185: 1307-1316; Venkatesha S H et al., 2011, The Journal of Biological Chemistry 286:15138-15146).

Distribution of Systemically Administered Liposomes In Vivo in Rats

ART-2-Cy7 liposomes and control-Cy7 liposomes (200 µM each) were used to study the bio-distribution of liposomes. The two types of liposomes of comparable fluorescence intensity were injected intravenously into arthritic or naïve (control) rats. Thereafter, real-time Near-infrared Fluorescence (NIRF) imaging was done employing the IVIS® Spectrum system (PerkinElmer) at two hourly intervals up to 6 h after injection. Rats were euthanized after 6 h time point, and different organs such as the heart, lung, spleen, liver, kidney and hind paws were harvested and subjected to ex vivo imaging (Heo R et al., 2017, Biomaterials 131:15-26).

DEX (Liposomal/Free) Treatment of Rats

Arthritis was induced in Lewis rats by injection of Mtb s.c. as described above. At the time of disease onset, these rats were randomized and assigned to 4 subgroups (n=5 per group) for intravenous (i.v.) injection (200 µL/rat) of ART-2-DEX liposomes, control-DEX liposomes lacking ART-2, free DEX or PBS (vehicle). These injections were performed on d 10, d 12, d 14 and d 16 after Mtb injection. The dose of DEX was 0.1 mg/kg body weight. Thereafter, rats were examined regularly and graded for arthritic severity as described above. After recording the arthritic scores, hind paws of rats were harvested and processed for histology.

The Profiles of Systemic Toxicity of Different Treatment Modalities

Blood samples were collected from the above mentioned rats (n=6/group) on d 20 following Mtb injection and serum was separated. These samples were then analyzed for serum chemistry (Charles River, Mass.) for the following: AST, aspartate aminotransferase; ALT, alanine transaminase; and TBIL (total bilirubin) for liver and biliary system toxicity; BUN, blood urea nitrogen, creatinine, and ratio of BUN versus creatinine for renal toxicity; lipase and amylase for pancreatic toxicity; and lactate dehydrogenase (LDH) for acute/chronic tissue damage.

Statistical Analysis

GraphPad Prism 6.0 was used to analyze and graph data of experiments. Analysis of variance (ANOVA), and where applicable, Wilcoxon rank-sum test were used for comparisons among multiple groups. Results were considered to be significant at P value below 0.05.

We claim:

1. A composition comprising at least one isolated peptide comprising the amino acid sequence CKPFDRALC (SEQ ID NO: 1), wherein the peptide selectively targets inflamed synovial tissue.

2. The composition of claim 1, wherein the composition further comprises a liposome, lipid, pharmaceutically acceptable carrier, or any combination thereof.

3. The composition of claim 1, wherein the peptide is conjugated to a liposome, lipid, pharmaceutically acceptable carrier, or any combination thereof.

4. The composition of claim 1, wherein the composition further comprises an agent selected from the group consisting of a protein, peptide, peptidomimetic, antibody, ribozyme, vector, nucleic acid molecule, antisense nucleic acid, small molecule drug, and any combination thereof.

5. The composition of claim 1, wherein the composition further comprises an agent selected from the group consisting of: a therapeutic agent, prophylactic agent, diagnostic agent, imaging agent, contrast agent, microparticle, nanoparticle, and any combination thereof.

6. The composition of claim 5, wherein the therapeutic agent is selected from the group consisting of a glucocorticoid, biologic, anti-arthritis drug, and any combination thereof.

7. The composition of claim 6, wherein the glucocorticoid is selected from the group consisting of cortisol (hydrocortisone), cortisone, prednisone, prednisolone, methylprednisolone, dexamethasone, betamethasone, triamcinolone, fludrocortisone acetate, deoxycorticosterone acetate, and any combination thereof.

8. The composition of claim 5, wherein the contrast agent is selected from the group consisting of radiocontrast medium, iodinated contrast agent, iodine, ipodate sodium, diatrizoate, metrizoate, iothalamate, ioxaglate, iopamidol, iohexol, ioxilan, iopromide, iodixanol, ioversol, barium, MRI contrast agent, gadolinium, ultrasound contrast agent, saline solution, and any combination thereof.

9. A method of delivering an agent to a biological tissue, the method comprising administering a composition to a subject in need thereof, wherein the composition comprises the agent and at least one isolated peptide comprising the amino acid sequence CKPFDRALC (SEQ ID NO: 1), and wherein the peptide selectively targets inflamed synovial tissue.

10. The method of claim 9, wherein the peptide is conjugated to a liposome, lipid, pharmaceutically acceptable carrier, or any combination thereof.

11. The method of claim 9, wherein the peptide is further conjugated to an agent selected from the group consisting of a therapeutic agent, prophylactic agent, diagnostic agent, imaging agent, contrast agent, microparticle, nanoparticle, and any combination thereof.

12. A method of treating a disease or disorder of a joint in a subject by delivery of an agent to a biological tissue of a subject, the method comprising administering the composition of claim 2 to a subject in need thereof.

13. The method of claim 12, wherein the peptide is conjugated to a liposome, lipid, pharmaceutically acceptable carrier, or any combination thereof.

14. The method of claim 12, wherein the peptide is further conjugated to an agent selected from the group consisting of a protein, peptide, peptidomimetic, antibody, ribozyme, vector, nucleic acid molecule, antisense nucleic acid, small molecule drug, and any combination thereof.

15. The method of claim 12, wherein the peptide is further conjugated to an agent selected from the group consisting of a therapeutic agent, prophylactic agent, diagnostic agent, imaging agent, contrast agent, microparticle, nanoparticle, and any combination thereof.

16. The method of claim 15, wherein the therapeutic agent is selected from the group consisting of a glucocorticoid, biologic, anti-arthritis drug, and any combination thereof.

17. The method of claim 16, wherein the glucocorticoid is selected from the group consisting of: cortisol (hydrocortisone), cortisone, prednisone, prednisolone, methylprednisolone, dexamethasone, betamethasone, triamcinolone, fludrocortisone acetate, deoxycorticosterone acetate, and any combination thereof.

18. The method of claim 12, wherein the disease or disorder is selected from the group consisting of: immune-mediated disease, autoimmune disease, inflammatory disease, autoinflammatory diseases, and any combination thereof.

19. The method of claim 12, wherein the disease or disorder is rheumatoid arthritis.

20. A method of diagnosing a disease or disorder of a joint in a subject by delivery of an agent to a biological tissue of a subject, the method comprising administering the composition of claim 2 to a subject in need thereof.

21. A method of imaging inflamed synovial tissue in a subject by delivery of an agent to a biological tissue of a subject, the method comprising administering the composition of claim 2 to a subject in need thereof.

22. A composition for targeted delivery of an agent, the composition comprising at least one isolated peptide conjugated to a liposome, lipid, pharmaceutically acceptable carrier, or any combination thereof, wherein the peptide is a tissue-targeting peptide comprising the amino acid sequence CKPFDRALC (SEQ ID NO: 1).

* * * * *